US011484250B2

(12) United States Patent
Udani et al.

(10) Patent No.: US 11,484,250 B2
(45) Date of Patent: Nov. 1, 2022

(54) SYSTEMS AND METHODS FOR IMPROVING CARTILAGE CONDUCTION TECHNOLOGY VIA FUNCTIONALLY GRADED MATERIALS

(71) Applicant: META PLATFORMS TECHNOLOGIES, LLC, Menlo Park, CA (US)

(72) Inventors: Janav Parag Udani, Redmond, WA (US); Morteza Khaleghimeybodi, Bothell, WA (US); Drew Stone Briggs, Seattle, WA (US); Peter Gottlieb, Seattle, WA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 155 days.

(21) Appl. No.: 16/752,922

(22) Filed: Jan. 27, 2020

(65) Prior Publication Data
US 2021/0228149 A1 Jul. 29, 2021

(51) Int. Cl.
| | |
|---|---|
| *H04R 25/00* | (2006.01) |
| *A61B 5/00* | (2006.01) |
| *B29C 64/386* | (2017.01) |
| *G02B 27/01* | (2006.01) |
| *H04R 1/10* | (2006.01) |

(52) U.S. Cl.
CPC .......... *A61B 5/4514* (2013.01); *B29C 64/386* (2017.08); *G02B 27/0101* (2013.01); *G02B 27/017* (2013.01); *H04R 1/1058* (2013.01); *G02B 2027/014* (2013.01);
(Continued)

(58) Field of Classification Search
CPC .... H04R 25/407; H04R 3/005; H04R 25/552; H04R 25/505; H04R 25/405; H04R 1/1016; H04R 25/604; H04R 2430/23
See application file for complete search history.

(56) References Cited

U.S. PATENT DOCUMENTS

| | | | |
|---|---|---|---|
| 2018/0234779 A1 | 8/2018 | Hsieh et al. | |
| 2020/0268260 A1* | 8/2020 | Tran | A61B 5/6817 |
| 2021/0297789 A1* | 9/2021 | De Haan | H04R 25/604 |

FOREIGN PATENT DOCUMENTS

| | | | | |
|---|---|---|---|---|
| EP | 0517497 A2 * | 3/1992 | | H04R 1/28 |
| EP | 0 517 497 A2 | 12/1992 | | |

(Continued)

OTHER PUBLICATIONS

International Search Report and Written Opinion received for PCT Application Serial No. PCT/US2021/012854 dated May 3, 2021, 11 pages.

(Continued)

*Primary Examiner* — Amir H Etesam
(74) *Attorney, Agent, or Firm* — FisherBroyles, LLP

(57) ABSTRACT

A cartilage conduction system may include (1) a transducer that generates mechanical energy and (2) a functionally graded material (FGM) interface dimensioned to be coupled between the transducer and cartilage located on an outer ear of a user, wherein the FGM interface (1) exhibits a gradation of at least one characteristic from one side of the FGM interface to another side of the FGM interface and (2) facilitates transferring the mechanical energy across the gradation of the characteristic from the transducer to the cartilage. Various other systems and methods are also disclosed.

19 Claims, 14 Drawing Sheets

(52) U.S. Cl.
CPC ........... *G02B 2027/0178* (2013.01); *H04R 2201/105* (2013.01); *H04R 2460/13* (2013.01); *H04R 2499/15* (2013.01)

(56) References Cited

FOREIGN PATENT DOCUMENTS

| | | |
|---|---|---|
| EP | 0517497 A2 | 12/1992 |
| WO | 2018/094538 A1 | 5/2018 |
| WO | 2018094538 A1 | 5/2018 |

OTHER PUBLICATIONS

Hosoi et al., "Cartilage conduction as the third pathway for sound transmission", Auris Nasus Larynx, vol. 46, No. 2, Apr. 1, 2019, 9 pages.

Zhang et al., "Functionally Graded Materials: An Overview of Stability, Buckling, and Free Vibration Analysis", Advances in Materials Science and Engineering, vol. 2019, Feb. 4, 2019, 18 pages.

Hosoi H., et al., "Cartilage Conduction as the Third Pathway for Sound Transmission," Auris Nasus Larynx, Apr. 1, 2019, vol. 46 (2), 9 Pages.

Zhang N., et al., "Functionally Graded Materials: An Overview of Stability, Buckling, and Free Vibration Analysis," Advances in Materials Science and Engineering, Feb. 4, 2019, vol. 2019, 18 Pages.

International Preliminary Report on Patentability for International Application No. PCT/US2021/012854, dated Aug. 11, 2022, 9 pages.

\* cited by examiner

SYSTEMS AND METHODS FOR IMPROVING CARTILAGE CONDUCTION TECHNOLOGY VIA FUNCTIONALLY GRADED MATERIALS

BRIEF DESCRIPTION OF DRAWINGS

The accompanying Drawings illustrate a number of exemplary embodiments and are parts of the specification. Together with the following description, the Drawings demonstrate and explain various principles of the instant disclosure.

Figure 1:
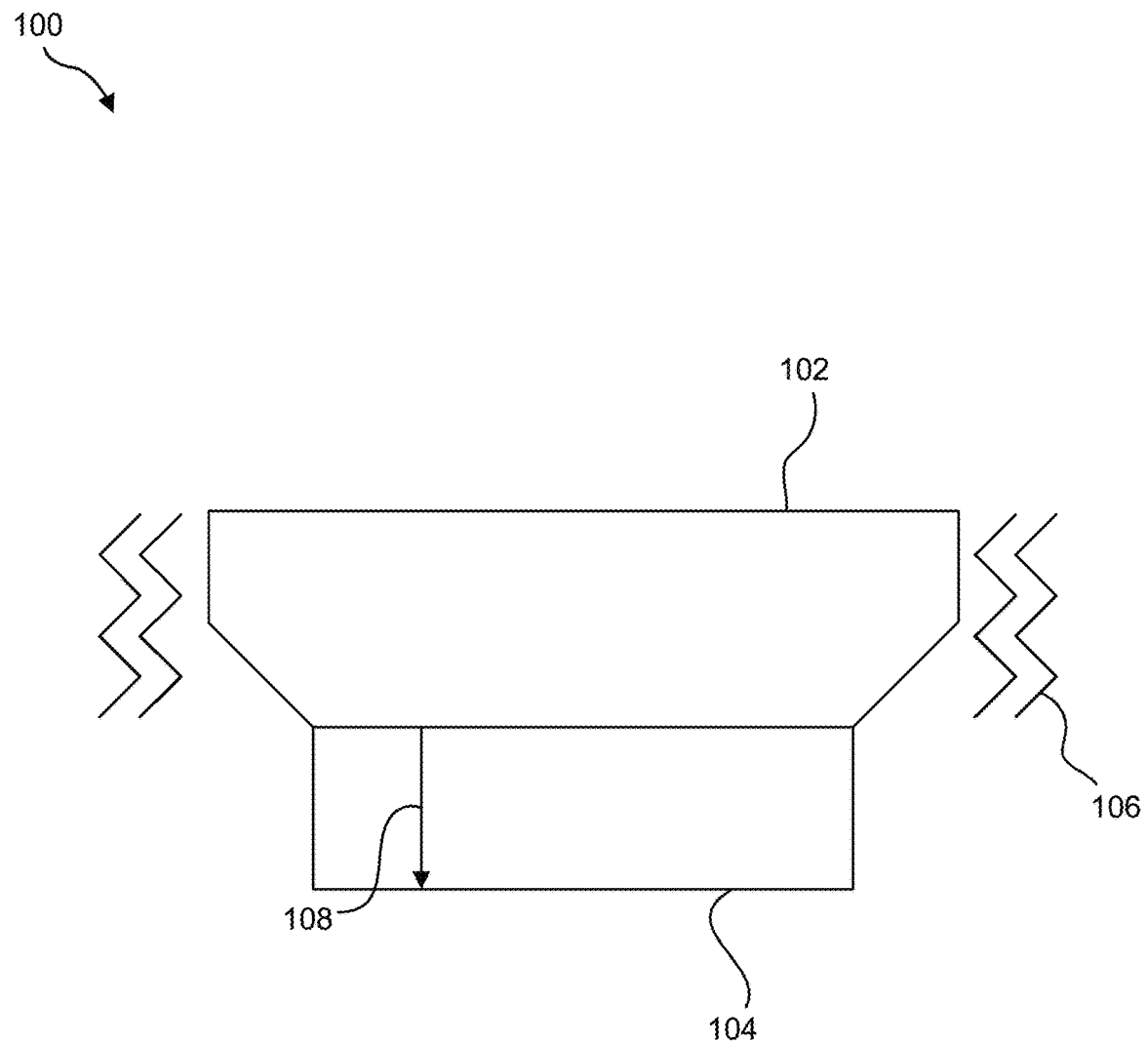
FIG. 1 is an illustration of an exemplary system for improving cartilage conduction technology via functionally graded materials (FGMs).

While the exemplary embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, combinations, equivalents, and alternatives falling within this disclosure.

DETAILED DESCRIPTION OF EXEMPLARY EMBODIMENTS

The present disclosure is generally directed to systems and methods for improving cartilage conduction technology via functionally graded materials (FGMs). As will be explained in greater detail below, these systems and methods may provide numerous features and benefits.

In some examples, cartilage conduction technology may involve exciting auricular cartilage located on an outer ear (sometimes referred to as the pinna) of a user. In such examples, the excitation of the cartilage may cause the cartilage to generate sound pressure that propagates through the user's ear canal toward the user's eardrum. Unfortunately, some cartilage conduction technologies may have certain drawbacks and/or design tradeoffs that give rise to one or more deficiencies. In other words, such cartilage conduction technologies may fail to provide a solution that addresses certain competing goals and/or objectives (e.g., high audio performance versus high user comfort).

For example, a cartilage conduction system may include a transducer that generates mechanical energy and an interface that couples the transducer to the outer ear of a user. In this example, to ensure that the interface is able to effectively and/or efficiently transfer the mechanical energy from the transducer to the user's outer ear, the interface may need to have a certain level of stiffness and/or damping and/or hardness (also known as mechanical impedance). Inappropriate selection of this stiffness and/or hardness of the interface may cause the user pain and/or discomfort when wearing the cartilage conduction system. As a result, the user may be dissuaded and/or discouraged from utilizing the cartilage conduction system for long periods of time.

One tradeoff of using a softer and/or more conformable material as the interface may be a decrease in the effectiveness and/or efficiency of the interface's energy transfer capabilities. For example, while a softer and/or more conformable interface between the transducer and the user's outer ear may support better user comfort, this softer and/or more conformable interface may be unable to effectively and/or efficiently transfer the mechanical energy from the transducer to the user's outer ear. As a result, the softer and/or more conformable interface may impair and/or harm the cartilage conduction system's audio performance.

The instant disclosure, therefore, identifies and addresses a need for systems and methods for improving cartilage conduction technology via FGMs. For example, as will be described in greater detail below, the various systems and methods disclosed herein may include and/or incorporate an FGM interface for coupling a transducer to cartilage located on the outer ear of a user. In this example, the FGM interface may exhibit a gradation of at least one characteristic (such as stiffness, hardness, loss factor or damping, density, lattice spacing, porosity, layer geometry and thickness, Poisson's ratio, and/or filler content) from one side to another. In other words, the gradation of the characteristic may constitute and/or represent a specific gradient of the characteristic across the FGM interface along one dimension and/or direction. By including and/or incorporating an FGM interface in this way, these systems and methods may be able to provide a cartilage conduction solution that achieves both high audio performance and high user comfort.

The following will provide, with reference to FIGS. 1-7, detailed descriptions of various systems, components, and/or implementations capable of improving cartilage conduction technology via FGMs. The discussion corresponding to FIG. 8 will provide detailed descriptions of an exemplary method for improving cartilage conduction technology via FGMs. The discussion corresponding to FIGS. 9-14 will provide detailed descriptions of types of exemplary artificial reality devices and/or systems that may facilitate and/or contribute to users' artificial reality experiences.

FIG. 1 illustrates an exemplary system 100 that improves cartilage conduction technology via FGMs. In some examples, system 100 may include and/or represent a cartilage conduction device, system, and/or technology. In one example, system 100 may be incorporated into and/or represent part of a wearable device. The terms "wearable" and "wearable device" may refer to any type or form of computing device that is worn by a user of an artificial reality system and/or visual display system as part of an article of clothing, an accessory, and/or an implant. Examples of wearable devices include, without limitation, headsets, headbands, head-mounted displays, glasses, frames, variations or combinations of one or more of the same, and/or any other suitable wearable devices.

As illustrated in FIG. 1, exemplary system 100 may include a transducer 102 that generates mechanical energy 106. In some examples, mechanical energy 106 generated by transducer 102 may include and/or represent vibrations, acoustic waves, and/or sound pressure. In one example, mechanical energy 106 may constitute and/or represent audio information and/or signals capable of being comprehended and/or discerned by a user of system 100. Additionally or alternatively, mechanical energy 106 may be converted, transformed, and/or modified by cartilage located on the user's outer ear to sound pressure capable of being comprehended and/or discerned by the user. Examples of transducer 102 include, without limitation, tactile transducers, loudspeakers, voice coil speakers, ribbon speakers, electrostatic speakers, piezoelectric transducers, electroacoustic transducers, cartilage conduction transducers, actuators, combinations or variations of one or more of the same, and/or any other suitable transducer.

Transducer 102 may have any suitable shape and/or size. In some examples, transducer 102 may be scaled to fit comfortably on and/or at the user's outer ear. In one example, transducer 102 may be smaller than a centimeter in length or diameter. Additionally or alternatively, transducer 102 may be smaller than 5 millimeters in length or diameter.

As illustrated in FIG. 1, exemplary system 100 may also include an FGM interface 104 dimensioned to be coupled between transducer 102 and cartilage located on the user's outer ear. In some examples, FGM interface 104 may be coupled to transducer 102 by any type or form of attachment mechanism. Additionally or alternatively, FGM interface 104 may be coupled to the user's outer ear by any type or form of attachment mechanism. Examples of such attachment mechanisms include, without limitation, adhesives (e.g., glues and/or silicones), sticky surfaces, fasteners, press-fit fastenings, interference-fit fastenings, friction-fit fastenings, slip-fit fastenings, magnetic fasteners, locks, pins, screws, joints, ties, clamps, clasps, stitching, staples, zippers, variations or combinations of one or more of the same, and/or any other suitable attachment mechanisms.

In some examples, FGM interface 104 may include and/or incorporate one or more FGMs. In one example, FGM interface 104 may exhibit a gradation 108 of at least one characteristic, attribute, quality, and/or property from one side and/or end of FGM interface 104 to another. In this example, FGM interface 104 may facilitate transferring mechanical energy 106 generated by transducer 102 across gradation 108 to the cartilage located on the user's outer ear. Examples of graded characteristics of FGM interface 104 include, without limitation, stiffness, hardness, modulus (e.g., Young's modulus), loss factor, density, lattice spacing, porosity, Poisson's ratio, filler content, variations or combinations of one or more of the same, and/or any other suitable characteristics.

In some examples, FGM interface 104 may include and/or incorporate multiple discrete material layers that collectively form, demonstrate, and/or manifest gradation 108 of the characteristic. Additionally or alternatively, FGM interface 104 may constitute and/or represent a specific continuous gradient (e.g., a linear gradient) of the characteristic from one side and/or end of FGM interface 104 to another. In one example, the specific continuous gradient of the characteristic may run, span, and/or extend along one dimension and/or in one direction of FGM interface 104. Alternatively, the different gradients of one or more characteristics may run, span, and/or extend along different dimensions and/or directions of FGM interface 104.

In some examples, FGM interface 104 may include and/or incorporate a variety of different materials. In one example, FGM interface 104 may include and/or incorporate one or more meta-materials that are man-made and/or engineered to exhibit certain characteristics that do not exist naturally. Additional examples of materials incorporated in FGM interface 104 include, without limitation, foams, polymers, composites, rubbers, papers, plastics, silicones, metals, corks, neoprenes, fiberglasses, polytetrafluorethylenes, elastomer gels, combinations or variations of one or more of the same, and/or any other suitable materials. In a certain embodiment, FGM interface 104 may include a mixture of silicone or elastomer gels with a proper mixing ratio. In this embodiment, the shore durometer of the silicone or elastomer mixture may be varied to create a material and/or structure with different stiffness, hardness, and/or damping characteristics.

In some examples, FGM interface 104 may include and/or have one side or end that is dimensioned for coupling to transducer 102. In such examples, FGM interface 104 may include and/or have another side or end that is dimensioned for coupling to cartilage located on the user's outer ear. In one example, the one side or end dimensioned for coupling to transducer 102 may exhibit and/or have a stiffness modulus that is above a certain minimum threshold and/or limit. In this example, the other side or end dimensioned for coupling to the user's outer ear may exhibit and/or have a stiffness modulus that is below a certain maximum threshold and/or limit. Accordingly, the side or end dimensioned for coupling to transducer 102 may be harder and/or stiffer than the side or end dimensioned for coupling to the user's outer ear. Put differently, the side or end dimensioned for coupling to the user's outer ear may be softer and/or more conformable than the side or end dimensioned for coupling to transducer 102.

In some examples, the side or end dimensioned for coupling to the user's outer ear may be malleable, flexible, moldable, and/or conformable to the shape of the user's outer ear. For example, the side or end dimensioned for coupling to the user's outer ear may contour to the cartilage located on the user's outer ear, thereby providing the user with a high level of comfort while wearing system 100. As a result, system 100 may constitute and/or represent a cartilage conduction solution and/or technology that achieves both high audio performance and high user comfort.

In some examples, FGM interface 104 may be manufactured, machined, and/or created in a variety of ways and/or contexts. For example, FGM interface 104 may be 3D-printed. Additionally or alternatively, FGM interface 104 may be assembled from a set of discrete material layers that are coupled together by any type or form of attachment mechanism, including any of those described above.

In some examples, FGM interface 104 may have and/or be formed into any suitable shape and/or size. Examples of such shapes include, without limitation, disks, cubes, cylinders, cuboids, spheres, variations or combinations of one or more of the same, and/or any other suitable shapes.

Figure 2:
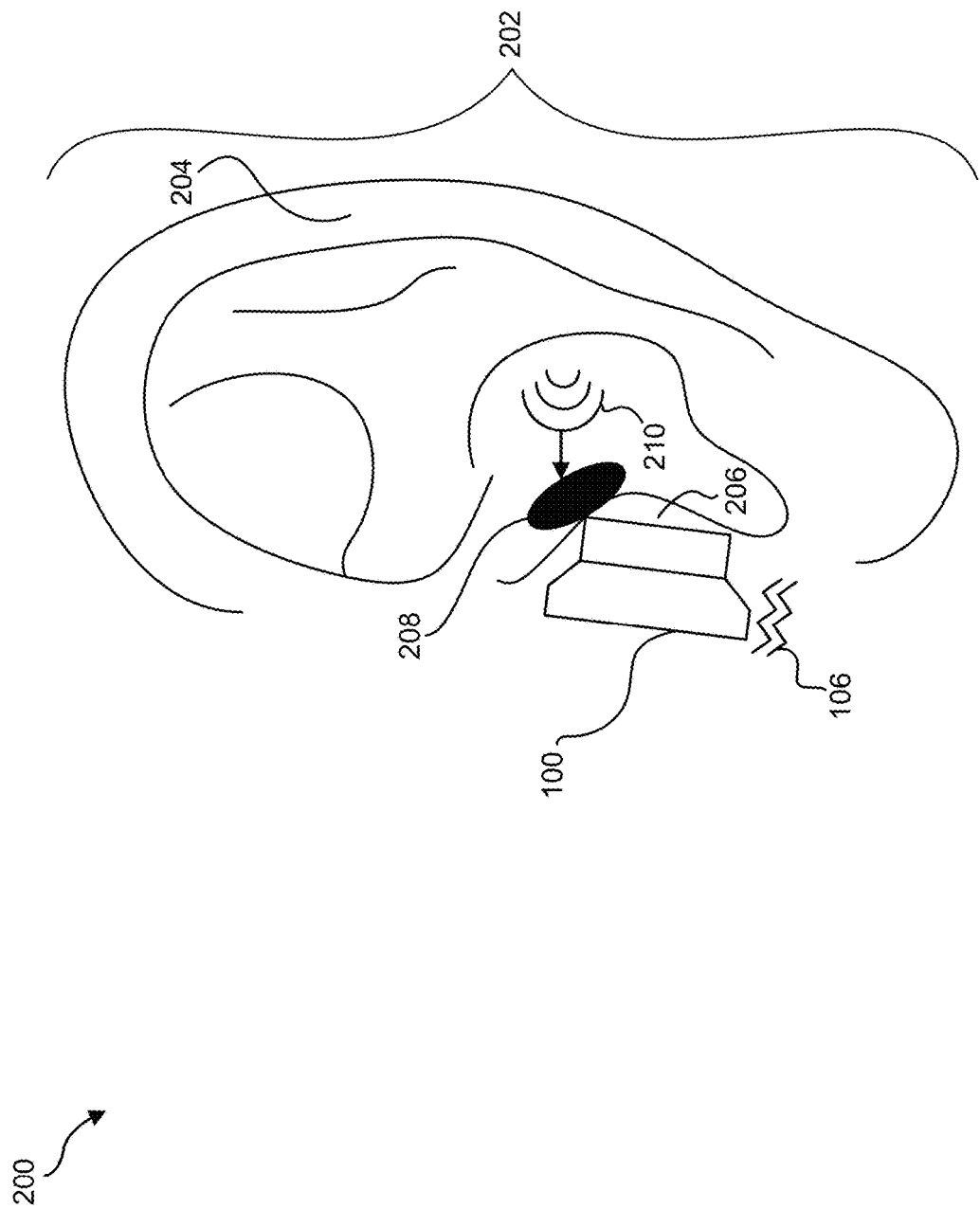
FIG. 2 is an illustration of an exemplary implementation of a system for improving cartilage conduction technology via FGMs.

FIG. 2 illustrates an exemplary implementation 200 of system 100 coupled and/or attached to an outer ear 202 of a user. In some examples, system 100 may be coupled and/or attached to any portion of outer ear 202 of the user, including the user's helix, tragus, antihelix, scapha, scaphoid fossa, concha, etc. As illustrated in FIG. 2, outer ear 202 of the user may include and/or represent a helix 204 and/or a tragus 206. In one example, implementation 200 may involve and/or represent system 100 being coupled and/or attached to tragus 206 of the user by FGM interface 104. In this example, transducer 102 may generate mechanical energy 106 that is transferred and/or carried to cartilage located on tragus 206 of the user. Accordingly, on the way from transducer 102 to tragus 206, mechanical energy 106 may cross, traverse, and/or pass through the characteristic gradation of FGM interface 104.

In one example, as mechanical energy 106 arrives at tragus 206 via FGM interface 104, the cartilage located on tragus 206 may convert and/or transform mechanical energy 106 to sound pressure 210 that propagates and/or passes through an ear canal 208 to the user's eardrum. In this example, sound pressure 210 may constitute and/or represent audio information and/or signals intended for listening and/or consumption by the user. Accordingly, the user may be able to listen to the audio information and/or signals represented in sound pressure 210.

Figure 3:
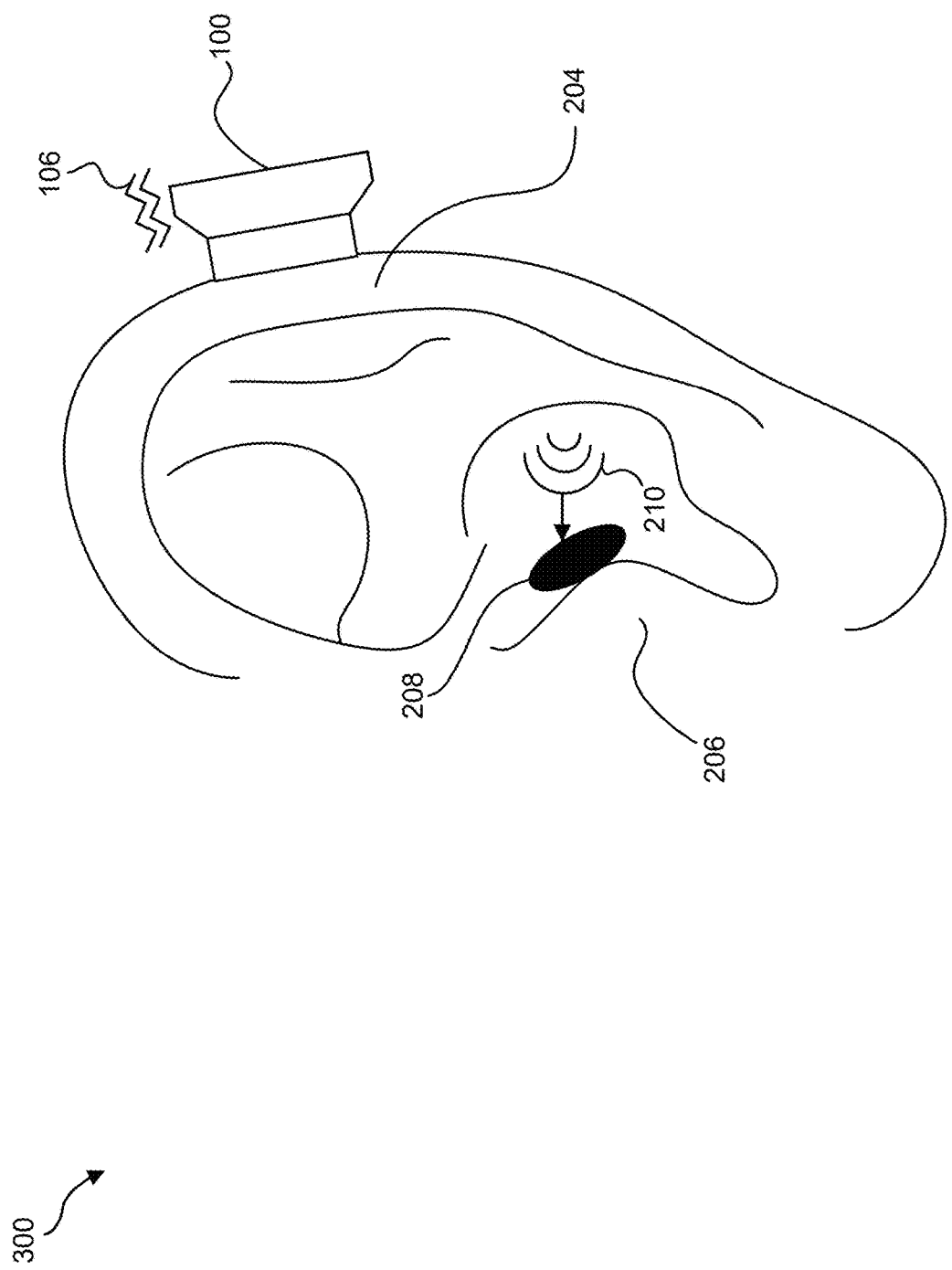
FIG. 3 is an illustration of an additional exemplary implementation of a system for improving cartilage conduction technology via FGMs.

FIG. 3 illustrates an additional exemplary implementation 300 of system 100 coupled and/or attached to an outer ear 202 of a user. As illustrated in FIG. 3, implementation 300 may involve and/or represent system 100 being coupled and/or attached to a helix 204 of the user by FGM interface 104. In this example, transducer 102 may generate mechanical energy 106 that is transferred and/or carried to cartilage located on helix 204 of the user. Accordingly, on the way from transducer 102 to helix 204, mechanical energy 106 may cross, traverse, and/or pass through the characteristic gradation of FGM interface 104.

In one example, as mechanical energy 106 arrives at helix 204 via FGM interface 104, the cartilage located on helix 204 may convert and/or transform mechanical energy 106 to sound pressure 210 that propagates and/or passes through an ear canal 208 to the user's eardrum. In this example, sound pressure 210 may constitute and/or represent audio information and/or signals intended for listening and/or consumption by the user. Accordingly, the user may be able to listen to the audio information and/or signals represented in sound pressure 210.

Figure 4:
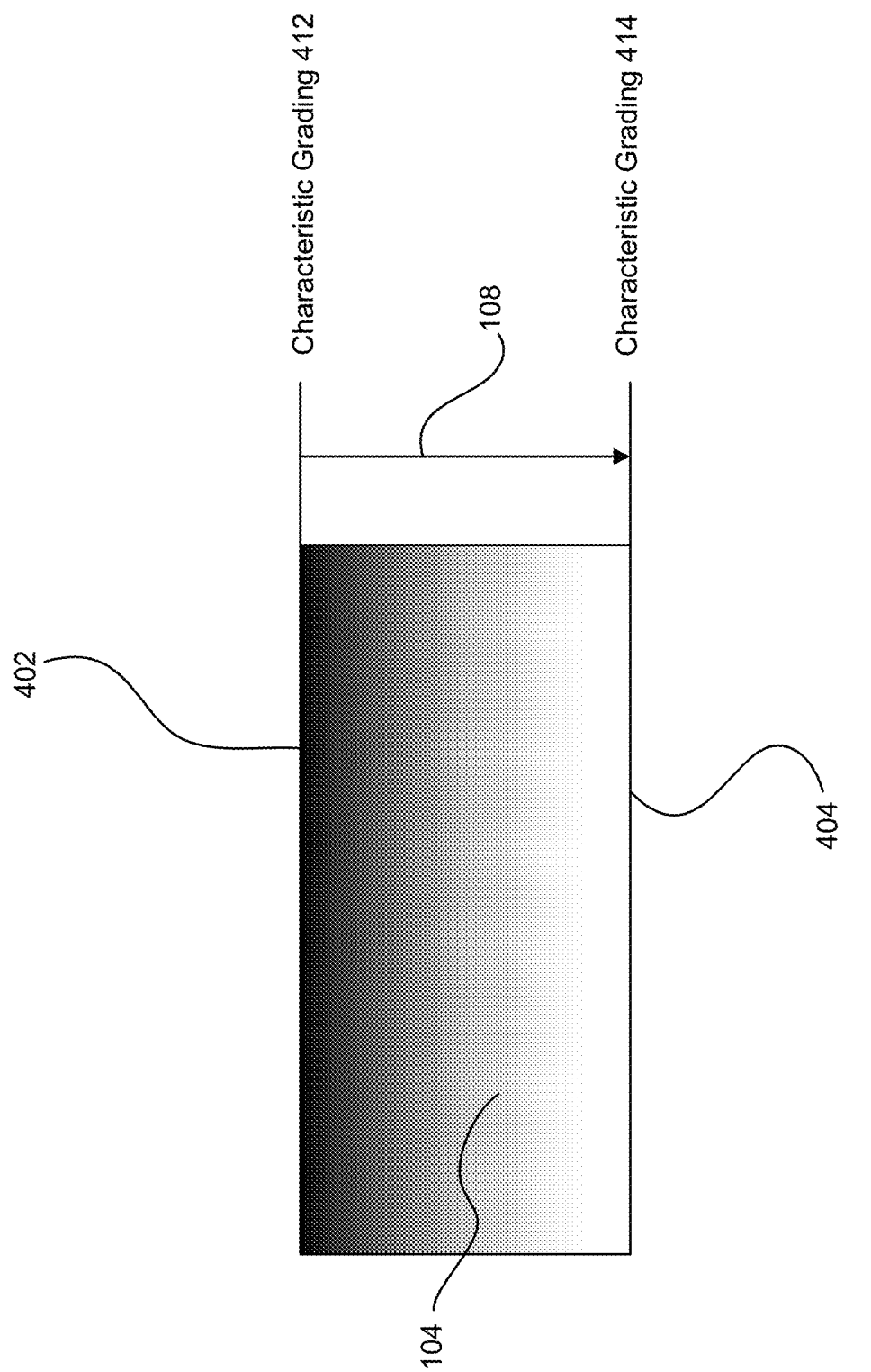
FIG. 4 is an illustration of an exemplary FGM interface that exhibits a continuous gradation of at least one characteristic from one side to another.

FIG. 4 illustrates an exemplary representation of FGM interface 104. As illustrated in FIG. 4, FGM interface 104 may include and/or represent a side 402 and a side 404. In one example, FGM interface 104 may exhibit, demonstrate, and/or manifest gradation 108 of at least one characteristic from side 402 to side 404. At side 402, FGM interface 104 may have a characteristic grading 412. In contrast, at side 404, FGM interface 104 may have a characteristic grading 414 that differs from characteristic grading 412. Accordingly, gradation 108 may include and/or represent a transition and/or transformation of one or more characteristics (such as stiffness, hardness, loss factor, density, lattice spacing, porosity, Poisson's ratio, and/or filler content) from side 402 to side 404.

As a specific example, characteristic grading 412 may represent a certain level of stiffness modulus at side 402 of FGM interface 104. Characteristic grading 414 may represent a different level of stiffness modulus at side 404 of FGM interface 104. In this example, characteristic grading 412 may correspond to a harder and/or stiffer modulus than characteristic grading 414. Put another way, characteristic grading 414 may correspond to a softer and/or more conformable modulus than characteristic grading 412. In certain embodiments, gradation 108 may continuously vary from side 402 to side 404.

Figure 5:
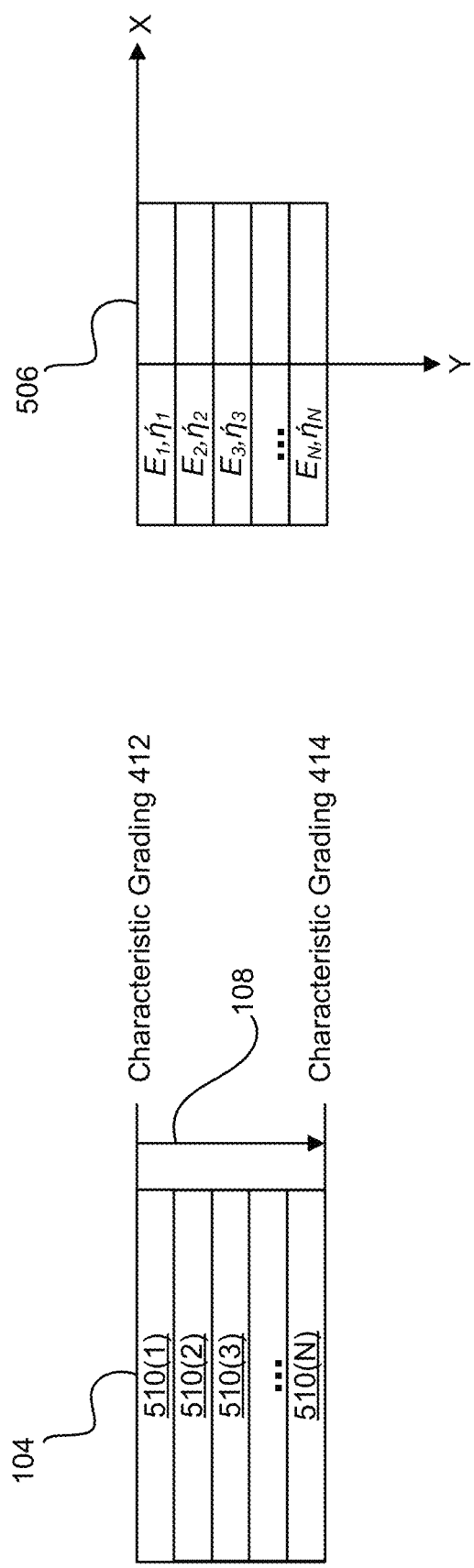
FIG. 5 is an illustration of an exemplary FGM interface that includes a plurality of discrete material layers that collectively form a gradation of at least one characteristic and an exemplary gradation graph that corresponds to the discreet material layers included in the FGM interface.

FIG. 5 illustrates an exemplary representation of FGM interface 104. As illustrated in FIG. 4, FGM interface 104 may include and/or represent a series of discrete material layers 510(1), 510(2), 510(3), and 510(N) (collectively referred to as discrete material layers 510(1)-(N)). As a whole, discrete material layers 510(1)-(N) may exhibit and/or form gradation 108 of one or more characteristic and/or properties. In one example, the characteristics and/or properties of discreet material layers 510(1)-(N) may be represented and/or characterized by a gradation graph 506 in FIG. 5.

As illustrated in FIG. 5, gradation graph 506 may represent discreet material layer 510(1) as having a composition and/or structure characterized by "$E_1, \acute{\eta}_1$". In this example, gradation graph 506 may also represent discreet material layer 510(2) as having a composition and/or structure characterized by "$E_2, \acute{\eta}_2$". Gradation graph 506 may further represent discreet material layer 510(3) as having a composition and/or structure characterized by "$E_3, \acute{\eta}_3$". In addition, gradation graph 506 may represent discreet material layer 510(4) as having a composition and/or structure characterized by "$E_4, \acute{\eta}_4$".

Figure 6:
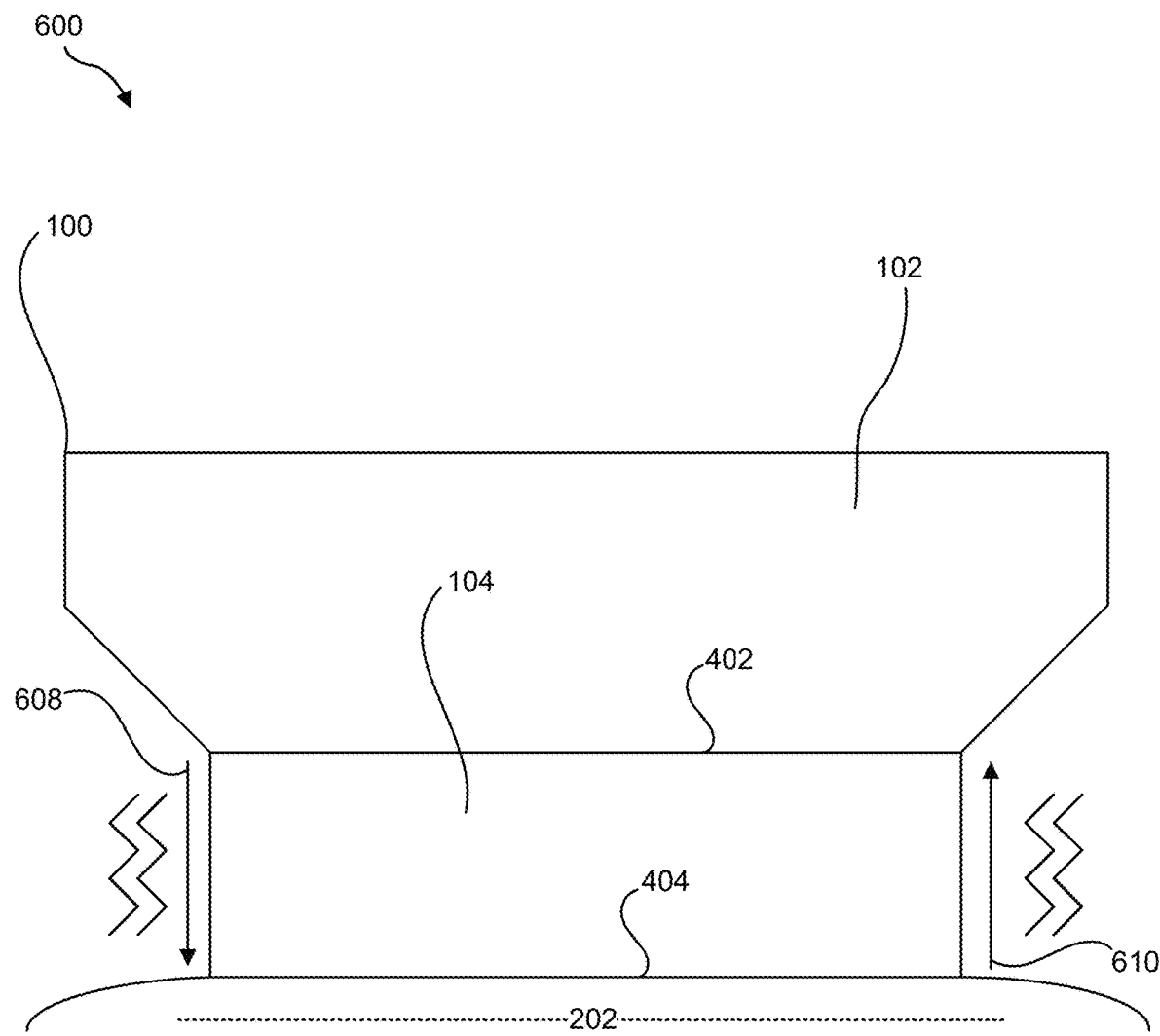
FIG. 6 is an illustration of an additional exemplary implementation of a system for improving cartilage conduction technology via FGMs.

FIG. 6 illustrates an additional exemplary implementation 600 of system 100 coupled and/or attached to outer ear 202 of a user. As illustrated in FIG. 6, FGM interface 104 may facilitate mechanically and/or audibly coupling transducer 102 to outer ear 202 of the user. In one example, transducer 102 may be coupled and/or attached to FGM interface 104 at side 402. In this example, outer ear 202 of the user may be coupled and/or attached to FGM interface 104 at side 404.

In some examples, FGM interface 104 may be anisotropic and/or unidirectional. In other words, FGM interface 104 may support and/or facilitate one-way communication and/or transfer of mechanical energy 106. Accordingly, FGM interface 104 may exhibit, demonstrate, and/or manifest one level of transmissibility in a direction 608 and another level of transmissibility in a direction 610. For example, FGM interface 104 may have high transmissibility in direction 608 but much less transmissibility in direction 610. In this example, FGM interface 104 may effectively and/or efficiently transfer, carry, and/or transmit mechanical energy 106 in direction 608 from transducer 102 to outer ear 202. However, FGM interface 104 may be unable to effectively and/or efficiently transfer, carry, and/or transmit mechanical energy 106 in direction 610 from outer ear 202 to transducer 102. Accordingly, FGM interface 104 may prevent at least some of mechanical energy 106 from returning to transducer 102 in direction 610 due at least in part to the transmissibility of direction 610 being less or lower than the transmissibility of direction 608.

In some examples, FGM interface 104 may efficiently couple mechanical energy 106 from transducer 102 to outer ear 202. Additionally or alternatively, FGM interface 104 may efficiently decouple and/or uncouple mechanical energy 106 from returning back to transducer 102. In other words, FGM interface 104 may efficiently prevent mechanical energy 106 from ricocheting and/or reflecting off outer ear 202 back toward transducer 102.

In some examples, FGM interface 104 may be impedance-matched at sides 402 and 404. For example, side 402 of FGM interface 104 may be impedance-matched to transducer 102. In this example, side 402 of FGM interface 104 and transducer 102 may have similar and/or identical impedances to one another. Additionally or alternatively, side 402 of FGM interface 104 and transducer 102 may have impedances that facilitate maximizing energy transfer and/or minimizing signal reflection.

In another example, side 404 of FGM interface 104 may be impedance-matched to outer ear 202. In this example, side 404 of FGM interface 104 and outer ear 202 may have similar and/or identical impedances to one another. Additionally or alternatively, side 404 of FGM interface 104 and outer ear 202 may have impedances that facilitate maximizing energy transfer and/or minimizing signal reflection.

Figure 7:
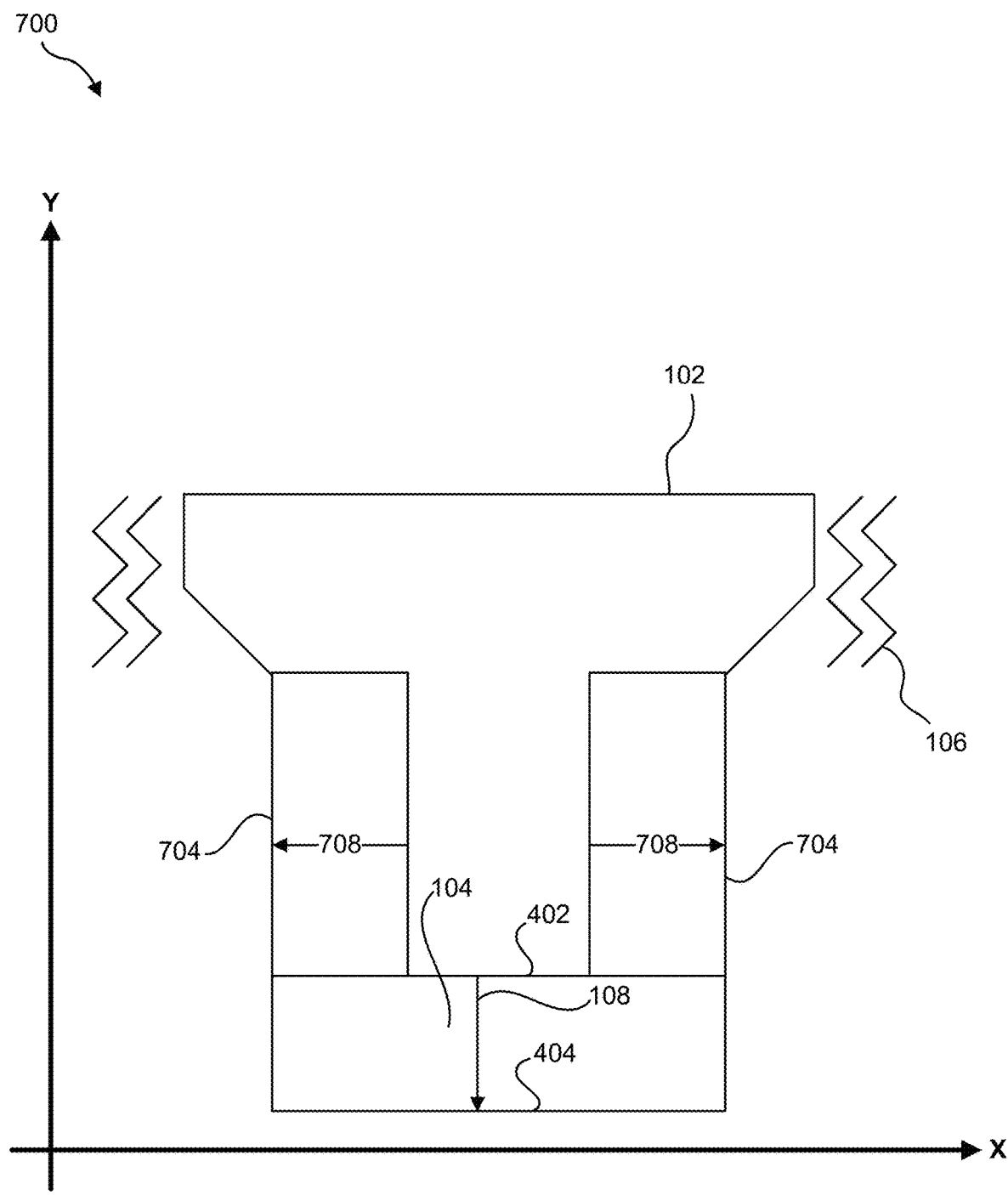
FIG. 7 is an illustration of an additional exemplary system for improving cartilage conduction technology via FGMs.

FIG. 7 illustrates an additional exemplary system 700 for improving cartilage conduction technology via FGMs. As illustrated in FIG. 7, exemplary system 700 may, like system 100 in FIG. 1, include transducer 102 that generates mechanical energy 106 and FGM interface 104 for coupling between transducer 102 and the outer ear of a user. However, unlike system 100 in FIG. 1, exemplary system 700 may also include an FGM suppressor 704 that at least partially encompasses a portion of transducer 102 coupled to FGM interface 104. In one example, FGM suppressor 704 and FGM interface 104 may represent, constitute, and/or form a single conjoined FGM unit. Alternatively, FGM suppressor 704 and FGM interface 104 may represent and/or constitute distinct or discrete FGM units that abut one another.

In some examples, FGM suppressor 704 and FGM interface 104 may share one or more characteristics in common, including any of those described above. Like FGM interface 104, FGM suppressor 704 may exhibit, demonstrate, and/or manifest a gradation 708 of one or more characteristics from one side to another. However, in one example, gradation 708 exhibited by FGM suppressor 704 and gradation 108 exhibited by FGM interface 104 may differ from one another. For example, relative to exemplary system 700 in FIG. 7, gradation 108 exhibited by FGM interface 104 may run, span, and/or extend along one dimension or direction (e.g., along the y-axis in FIG. 7), whereas gradation 708 exhibited by FGM suppressor 704 may run, span, and/or extend along another dimension or direction (e.g., along the x-axis in FIG. 7). Additionally or alternatively, FGM suppressor 704 and FGM interface 104 may have differing characteristic and/or property gradings relative to one another.

In some examples, FGM suppressor 704 may mitigate and/or reduce leakage of mechanical energy 106 generated by transducer 102 to the user's environment and/or the surrounding air. In doing so, FGM suppressor 704 may increase user privacy by containing and/or suppressing mechanical energy 106 to the user's personal space. In one example, gradation 708 exhibited by FGM suppressor 704 and/or gradation 108 exhibited by FGM interface 104 may be designed and/or oriented to improve and/or maximize such privacy.

In one example, gradation 708 exhibited by FGM suppressor 704 may constitute and/or represent a specific gradient (e.g., a linear gradient) of loss factor from one side and/or end of FGM suppressor 704 to another. In this example, the specific gradient of loss factor may run, span, and/or extend along one dimension and/or in one direction (e.g., along the x-axis in FIG. 7) of FGM suppressor 704.

In some examples, FGM suppressor 704 may have and/or be formed into any suitable shape and/or size. Examples of such shapes include, without limitation, disks, cubes, cylinders, cuboids, spheres, variations or combinations of one or more of the same, and/or any other suitable shapes.

Figure 8:
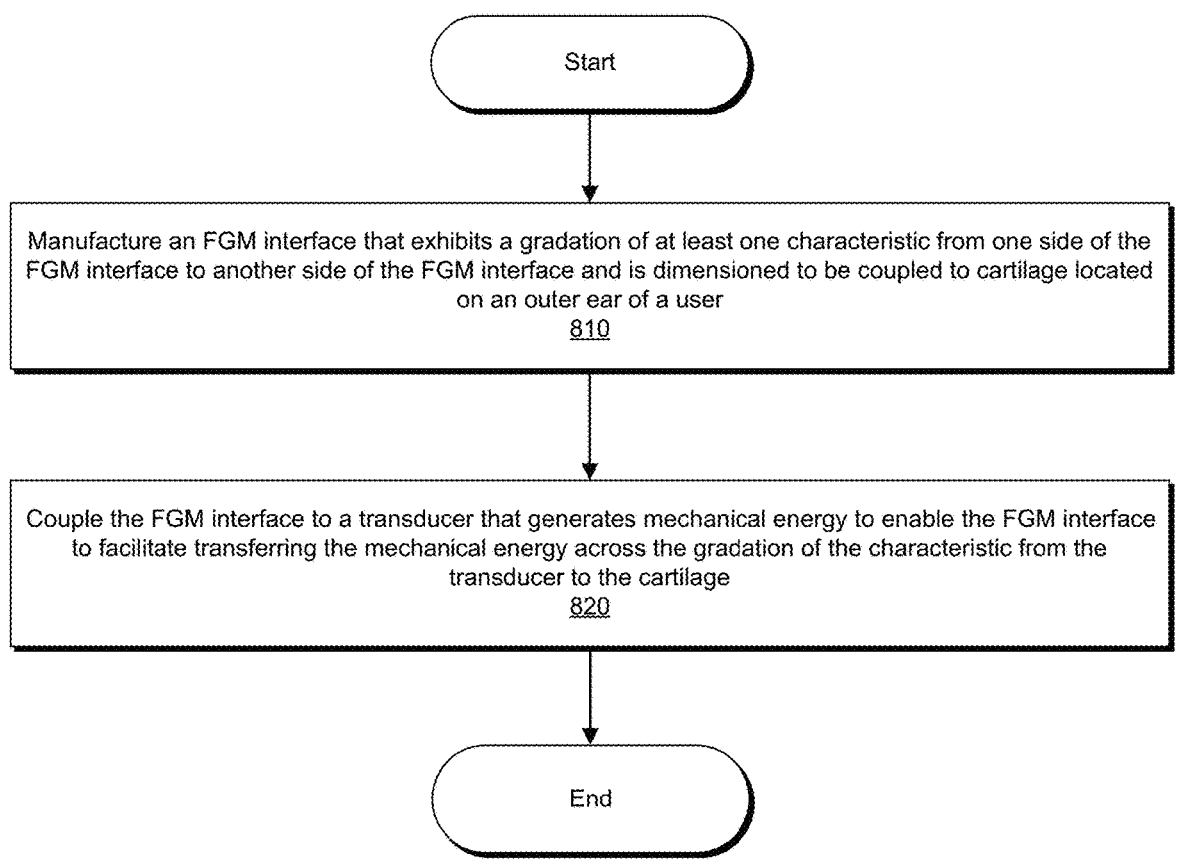
FIG. 8 is a flowchart of an exemplary method for improving cartilage conduction technology via FGMs.

FIG. 8 is a flow diagram of an exemplary method 800 for improving cartilage conduction technology via FGMs. In one example, the steps shown in FIG. 8 may be performed as part of assembling and/or manufacturing a cartilage conduction system. Additionally or alternatively, the steps shown in FIG. 8 may also incorporate and/or involve various sub-steps and/or variations consistent with the descriptions provided above in connection with FIGS. 1-7.

As illustrated in FIG. 8, method 800 may include a step 810 in which an FGM interface is manufactured. In one example, a computing equipment manufacturer or subcontractor may create, construct, and/or fabricate the FGM interface. For example, the computing equipment manufacturer or subcontractor may 3D-print the FGM interface. In this example, the FGM interface may exhibit a gradation of one or more characteristics from one side to another. Additionally or alternatively, the FGM interface may be dimensioned for coupling to cartilage located on an outer ear of a user.

As illustrated in FIG. 8, method 800 may include a step 820 in which the FGM interface is coupled to a transducer that generates mechanical energy. In one example, the computing equipment manufacturer or subcontractor may couple, attach, and/or adhere the FGM interface to the transducer. For example, the computing equipment manufacturer or subcontractor may couple the FGM interface to the transducer with an adhesive (such as silicone). In some examples, this coupling between the FGM interface and the transducer may enable the FGM interface to transfer and/or carry the mechanical energy across the gradation of the characteristic(s) from the transducer to the cartilage located on the user's outer ear.

As described above in connection with FIGS. 1-8, a cartilage conduction system may include a transducer that generates vibrations and an FGM interface coupled between the transducer and a user's pinna. In some examples, the FGM interface may have a property grading from one side to another. In such examples, the FGM interface may transfer and/or carry the vibrations generated by the transducer across the property grading to the user's pinna. As the vibrations arrive at the user's pinna, cartilage may convert the vibrations to sound pressure that then traverses the user's ear canal toward his or her ear drum for consumption and/or listening.

In some examples, the FGM interface may couple the vibrations to the user's pinna and/or decouple the vibrations that arrive at the user's pinna from the transducer. In such examples, the FGM interface may avoid unnecessarily attenuating the vibrations passing from the transducer to the user's pinna. Accordingly, the FGM interface may facilitate unidirectional delivery of the vibrations generated by the transducer.

In some examples, the FGM interface may include and/or represent a series of composite materials whose microstructures vary from one to the next. This variation of microstructures may effectively tune the properties of the FGM interface to satisfy traditionally competing requirements (e.g., high audio performance and high user comfort) of the cartilage conduction system.

The FGM interface may take a variety of different forms. For example, the FGM interface may include and/or represent standard FGMs with regular geometries that feature property gradation along a single dimension and/or direction. Alternatively, the FGM interface may include and/or represent irregular FGMs with complex geometries that feature different property gradations along different dimensions and/or directions. These irregular FGMs may support and/or facilitate unidirectional coupling of vibrations from the transducer to the user's pinna. Additionally or alternatively, these irregular FGMs may minimize the leakage of sound and/or noise to the user's environment, thereby improving and/or increasing the user's privacy. One way of minimizing such leakage may be to incrementally grade the loss factor of the side walls (e.g., FGM suppressor 704 in FIG. 7) to make them more lossy. These lossy side walls may effectively minimize the transmissibility of vibrations to the user's environment. Finally, the FGM interface may include and/or incorporate certain man-made and/or engineered meta-materials that do not occur in nature.

EXAMPLE EMBODIMENTS

Example 1: A cartilage conduction system comprising (1) a transducer that generates mechanical energy and (2) a functionally graded material (FGM) interface dimensioned to be coupled between the transducer and cartilage located on an outer ear of a user, wherein the FGM interface (1) exhibits a gradation of at least one characteristic from one side of the FGM interface to another side of the FGM interface and (2) facilitates transferring the mechanical energy across the gradation of the characteristic from the transducer to the cartilage.

Example 2: The cartilage conduction system of Example 1, wherein the FGM interface comprises a plurality of discrete material layers that collectively form the gradation of the characteristic exhibited by the FGM interface.

Example 3: The cartilage conduction system of Example 1, wherein the gradation of the characteristic exhibited by the FGM interface comprises a specific gradient of the characteristic from the one side to the another side along one dimension of the FGM interface.

Example 4: The cartilage conduction system of Example 1, wherein the characteristic comprises at least one of stiffness, loss factor, density, lattice spacing, porosity, Poisson's ratio, or filler content.

Example 5: The cartilage conduction system of Example 1, wherein (1) the one side of the FGM interface is coupled to the transducer, (2) the another side of the FGM interface is dimensioned to be coupled to the cartilage located on the outer ear of the user, (3) the one side of the FGM interface has a first stiffness modulus, and (4) the another side of the FGM interface has a second stiffness modulus that is lower than the first stiffness modulus.

Example 6: The cartilage conduction system of Example 5, wherein the another side of the FGM interface contours to the cartilage located on the outer ear of the user.

Example 7: The cartilage conduction system of Example 6, wherein (1) the one side is impedance-matched to the transducer and (2) the another side is impedance-matched to the cartilage located on the outer ear of the user.

Example 8: The cartilage conduction system of Example 6, wherein the FGM interface is dimensioned to be coupled between the transducer and at least one of (1) a portion of a helix of the user or (2) a tragus of the user.

Example 9: The cartilage conduction system of Example 1, wherein the transducer generates vibrations that (1) are transferred to the cartilage located on the outer ear of the user via the FGM interface and (2) cause the cartilage to generate sound pressure that propagates to an eardrum of the user.

Example 10: The cartilage conduction system of Example 1, wherein the FGM interface is anisotropic such that (1) the FGM interface exhibits a first level of transmissibility in a direction from the transducer to the cartilage and (2) the FGM interface exhibits a second level of transmissibility in an opposite direction from the cartilage to the transducer, the second level of transmissibility being lower than the first level of transmissibility.

Example 11: The cartilage conduction system of Example 10, wherein (1) the mechanical energy comprises vibrations, (2) the cartilage generates sound pressure from the vibrations, and (3) the FGM interface prevents at least some of the vibrations from returning to the transducer in the opposite direction due at least in part to the second level of transmissibility being lower than the first level of transmissibility.

Example 12: The cartilage conduction system of Example 1, further comprising an FGM suppressor that at least partially encompasses a portion of the transducer coupled to the FGM interface, wherein the FGM suppressor (1) exhibits an additional gradation of at least one characteristic from one side of the FGM suppressor to another side of the FGM suppressor and (2) mitigates leakage of the mechanical energy generated by the transducer to an environment of the user.

Example 13: The cartilage conduction system of Example 12, wherein the gradation of the characteristic exhibited by the FGM interface and the additional gradation of the characteristic exhibited by the FGM suppressor differ from one another.

Example 14: The cartilage conduction system of claim 12, wherein the additional gradation of the characteristic exhibited by the FGM suppressor comprises a specific gradient of loss factor from the one side of the FGM suppressor to the another side of the FGM suppressor along one dimension.

Example 15: The cartilage conduction system of Example 1, wherein the FGM interface is 3D-printed.

Example 16: An artificial reality system comprising (1) a head-mounted display and (2) a cartilage conduction device communicatively coupled to the head-mounted display, wherein the cartilage conduction device comprises (1) a transducer that generates mechanical energy and (2) a functionally graded material (FGM) interface dimensioned to be coupled between the transducer and cartilage located on an outer ear of a user, wherein the FGM interface (1) exhibits a gradation of at least one characteristic from one side of the FGM interface to another side of the FGM interface and (2) facilitates transferring the mechanical energy across the gradation of the characteristic from the transducer to the cartilage.

Example 17: The artificial reality system of Example 16, wherein the FGM interface comprises a plurality of discrete material layers that form the structural gradation of the FGM interface.

Example 18: The artificial reality system of Example 16, wherein the gradation of the characteristic exhibited by the FGM interface comprises a specific gradient of the characteristic from the one side to the another side along one dimension of the FGM interface.

Example 19: The artificial reality system of Example 16, wherein the characteristic comprises at least one of stiffness, loss factor, density, lattice spacing, porosity, Poisson's ratio, or filler content.

Example 20: A method comprising (1) manufacturing a functionally graded material (FGM) interface that (A) exhibits a gradation of at least one characteristic from one side of the FGM interface to another side of the FGM interface and (B) is dimensioned to be coupled to cartilage located on an outer ear of a user and (2) coupling the FGM interface to a transducer that generates mechanical energy to enable the FGM interface to facilitate transferring the mechanical energy across the gradation of the characteristic from the transducer to the cartilage.

The preceding description has been provided to enable others skilled in the art to best utilize various aspects of the exemplary embodiments disclosed herein. This exemplary description is not intended to be exhaustive or to be limited to any precise form disclosed. Many modifications and variations are possible without departing from the spirit and scope of the instant disclosure. The embodiments disclosed herein should be considered in all respects illustrative and not restrictive. Reference should be made to the appended claims and their equivalents in determining the scope of the instant disclosure.

Embodiments of the present disclosure may include or be implemented in conjunction with various types of artificial reality systems. Artificial reality is a form of reality that has been adjusted in some manner before presentation to a user, which may include, e.g., a virtual reality, an augmented reality, a mixed reality, a hybrid reality, or some combination and/or derivative thereof. Artificial reality content may include completely generated content or generated content combined with captured (e.g., real-world) content. The artificial reality content may include video, audio, haptic feedback, or some combination thereof, any of which may be presented in a single channel or in multiple channels (such as stereo video that produces a three-dimensional (3D) effect to the viewer). Additionally, in some embodiments, artificial reality may also be associated with applications, products, accessories, services, or some combination thereof, that are used to, e.g., create content in an artificial reality and/or are otherwise used in (e.g., to perform activities in) an artificial reality.

Artificial reality systems may be implemented in a variety of different form factors and configurations. Some artificial reality systems may be designed to work without near-eye displays (NEDs), an example of which is augmented reality system 900 in FIG. 9. Other artificial reality systems may include an NED that also provides visibility into the real world (e.g., augmented reality system 1000 in FIG. 10) or that visually immerses a user in an artificial reality (e.g., virtual reality system 1100 in FIG. 11). While some artificial reality devices may be self-contained systems, other artificial reality devices may communicate and/or coordinate with external devices to provide an artificial reality experience to a user. Examples of such external devices include handheld controllers, mobile devices, desktop computers, devices worn by a user, devices worn by one or more other users, and/or any other suitable external system.

Figure 9:
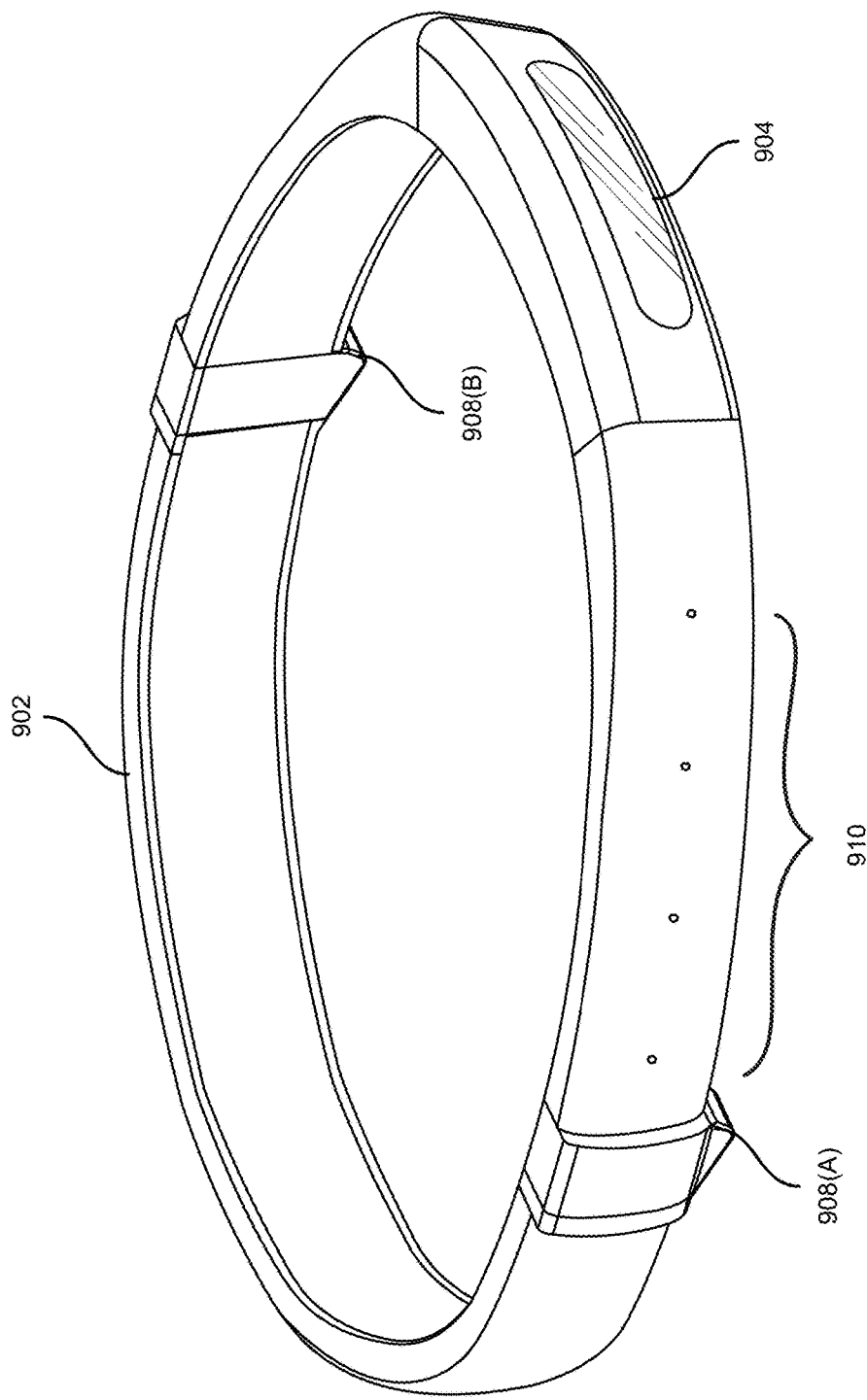
FIG. 9 is an illustration of an exemplary artificial reality headband that may be used in connection with embodiments of this disclosure.

Turning to FIG. 9, augmented reality system 900 generally represents a wearable device dimensioned to fit about a body part (e.g., a head) of a user. As shown in FIG. 9, system 900 may include a frame 902 and a camera assembly 904 that is coupled to frame 902 and configured to gather information about a local environment by observing the local environment. Augmented reality system 900 may also include one or more audio devices, such as output audio transducers 908(A) and 908(B) and input audio transducers 910. Output audio transducers 908(A) and 908(B) may provide audio feedback and/or content to a user, and input audio transducers 910 may capture audio in a user's environment.

As shown, augmented reality system 900 may not necessarily include an NED positioned in front of a user's eyes. Augmented reality systems without NEDs may take a variety of forms, such as head bands, hats, hair bands, belts, watches, wrist bands, ankle bands, rings, neckbands, necklaces, chest bands, eyewear frames, and/or any other suitable type or form of apparatus. While augmented reality system 900 may not include an NED, augmented reality system 900 may include other types of screens or visual feedback devices (e.g., a display screen integrated into a side of frame 902).

Figure 10:
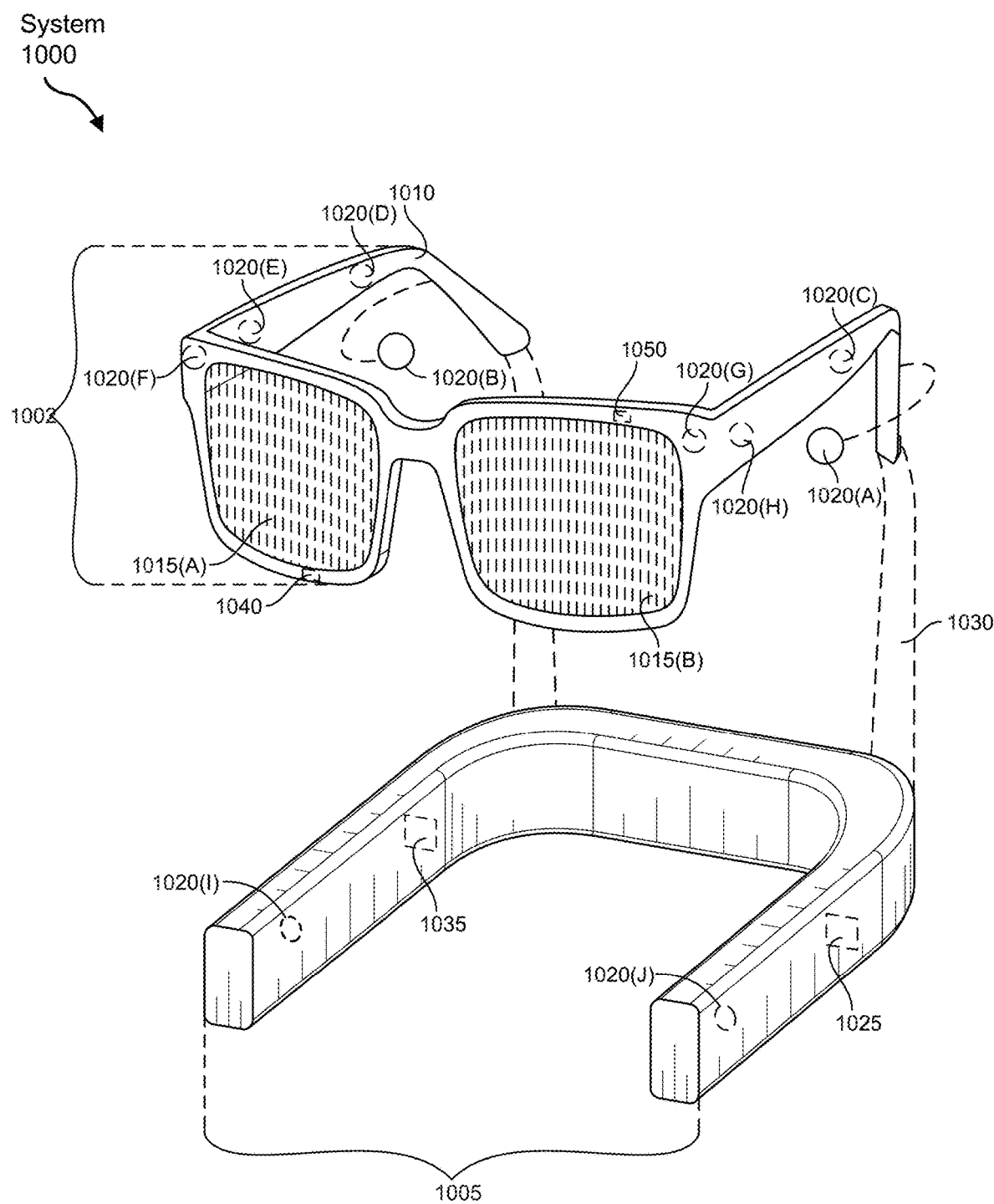
FIG. 10 is an illustration of exemplary augmented reality glasses that may be used in connection with embodiments of this disclosure.

The embodiments discussed in this disclosure may also be implemented in augmented reality systems that include one or more NEDs. For example, as shown in FIG. 10, augmented reality system 1000 may include an eyewear device 1002 with a frame 1010 configured to hold a left display device 1015(A) and a right display device 1015(B) in front of a user's eyes. Display devices 1015(A) and 1015(B) may act together or independently to present an image or series of images to a user. While augmented reality system 1000 includes two displays, embodiments of this disclosure may be implemented in augmented reality systems with a single NED or more than two NEDs.

In some embodiments, augmented reality system 1000 may include one or more sensors, such as sensor 1040. Sensor 1040 may generate measurement signals in response to motion of augmented reality system 1000 and may be located on substantially any portion of frame 1010. Sensor 1040 may represent a position sensor, an inertial measurement unit (IMU), a depth camera assembly, or any combination thereof. In some embodiments, augmented reality system 1000 may or may not include sensor 1040 or may include more than one sensor. In embodiments in which sensor 1040 includes an IMU, the IMU may generate calibration data based on measurement signals from sensor 1040. Examples of sensor 1040 may include, without limitation, accelerometers, gyroscopes, magnetometers, other suitable types of sensors that detect motion, sensors used for error correction of the IMU, or some combination thereof.

Augmented reality system 1000 may also include a microphone array with a plurality of acoustic transducers 1020 (A)-1020(J), referred to collectively as acoustic transducers 1020. Acoustic transducers 1020 may be transducers that detect air pressure variations induced by sound waves. Each acoustic transducer 1020 may be configured to detect sound and convert the detected sound into an electronic format (e.g., an analog or digital format). The microphone array in FIG. 2 may include, for example, ten acoustic transducers: 1020(A) and 1020(B), which may be designed to be placed inside a corresponding ear of the user, acoustic transducers 1020(C), 1020(D), 1020(E), 1020(F), 1020(G), and 1020 (H), which may be positioned at various locations on frame 1010, and/or acoustic transducers 1020(I) and 1020(J), which may be positioned on a corresponding neckband 1005.

In some embodiments, one or more of acoustic transducers 1020(A)-(F) may be used as output transducers (e.g., speakers). For example, acoustic transducers 1020(A) and/ or 1020(B) may be earbuds or any other suitable type of headphone or speaker.

The configuration of acoustic transducers 1020 of the microphone array may vary. While augmented reality system 1000 is shown in FIG. 10 as having ten acoustic transducers 1020, the number of acoustic transducers 1020 may be greater or less than ten. In some embodiments, using higher numbers of acoustic transducers 1020 may increase the amount of audio information collected and/or the sensitivity and accuracy of the audio information. In contrast, using a lower number of acoustic transducers 1020 may decrease the computing power required by an associated controller 1050 to process the collected audio information. In addition, the position of each acoustic transducer 1020 of the microphone array may vary. For example, the position of an acoustic transducer 1020 may include a defined position on the user, a defined coordinate on frame 1010, an orientation associated with each acoustic transducer 1020, or some combination thereof.

Acoustic transducers 1020(A) and 1020(B) may be positioned on different parts of the user's ear, such as behind the pinna or within the auricle or fossa. Or, there may be additional acoustic transducers 1020 on or surrounding the ear in addition to acoustic transducers 1020 inside the ear canal. Having an acoustic transducer 1020 positioned next to an ear canal of a user may enable the microphone array to collect information on how sounds arrive at the ear canal. By positioning at least two of acoustic transducers 1020 on either side of a user's head (e.g., as binaural microphones), augmented reality device 1000 may simulate binaural hearing and capture a 3D stereo sound field around about a user's head. In some embodiments, acoustic transducers 1020(A) and 1020(B) may be connected to augmented reality system 1000 via a wired connection 1030, and in other embodiments, acoustic transducers 1020(A) and 1020(B) may be connected to augmented reality system 1000 via a wireless connection (e.g., a Bluetooth connection). In still other embodiments, acoustic transducers 1020(A) and 1020(B) may not be used at all in conjunction with augmented reality system 1000.

Acoustic transducers 1020 on frame 1010 may be positioned along the length of the temples, across the bridge, above or below display devices 1015(A) and 1015(B), or some combination thereof. Acoustic transducers 1020 may be oriented such that the microphone array is able to detect sounds in a wide range of directions surrounding the user wearing the augmented reality system 1000. In some embodiments, an optimization process may be performed during manufacturing of augmented reality system 1000 to determine relative positioning of each acoustic transducer 1020 in the microphone array.

In some examples, augmented reality system 1000 may include or be connected to an external device (e.g., a paired device), such as neckband 1005. Neckband 1005 generally represents any type or form of paired device. Thus, the following discussion of neckband 1005 may also apply to various other paired devices, such as charging cases, smart watches, smart phones, wrist bands, other wearable devices, hand-held controllers, tablet computers, laptop computers and other external compute devices, etc.

As shown, neckband 1005 may be coupled to eyewear device 1002 via one or more connectors. The connectors may be wired or wireless and may include electrical and/or non-electrical (e.g., structural) components. In some cases, eyewear device 1002 and neckband 1005 may operate independently without any wired or wireless connection between them. While FIG. 10 illustrates the components of eyewear device 1002 and neckband 1005 in example locations on eyewear device 1002 and neckband 1005, the components may be located elsewhere and/or distributed differently on eyewear device 1002 and/or neckband 1005. In some embodiments, the components of eyewear device 1002 and neckband 1005 may be located on one or more additional peripheral devices paired with eyewear device 1002, neckband 1005, or some combination thereof.

Pairing external devices, such as neckband 1005, with augmented reality eyewear devices may enable the eyewear devices to achieve the form factor of a pair of glasses while still providing sufficient battery and computation power for expanded capabilities. Some or all of the battery power, computational resources, and/or additional features of augmented reality system 1000 may be provided by a paired device or shared between a paired device and an eyewear device, thus reducing the weight, heat profile, and form factor of the eyewear device overall while still retaining desired functionality. For example, neckband 1005 may allow components that would otherwise be included on an eyewear device to be included in neckband 1005 since users may tolerate a heavier weight load on their shoulders than they would tolerate on their heads. Neckband 1005 may also have a larger surface area over which to diffuse and disperse heat to the ambient environment. Thus, neckband 1005 may allow for greater battery and computation capacity than might otherwise have been possible on a stand-alone eyewear device. Since weight carried in neckband 1005 may be less invasive to a user than weight carried in eyewear device 1002, a user may tolerate wearing a lighter eyewear device and carrying or wearing the paired device for greater lengths of time than a user would tolerate wearing a heavy stand-alone eyewear device, thereby enabling users to more fully incorporate artificial reality environments into their day-to-day activities.

Neckband 1005 may be communicatively coupled with eyewear device 1002 and/or to other devices. These other devices may provide certain functions (e.g., tracking, localizing, depth mapping, processing, storage, etc.) to augmented reality system 1000. In the embodiment of FIG. 10, neckband 1005 may include two acoustic transducers (e.g., 1020(I) and 1020(J)) that are part of the microphone array (or potentially form their own microphone subarray). Neckband 1005 may also include a controller 1025 and a power source 1035.

Acoustic transducers 1020(I) and 1020(J) of neckband 1005 may be configured to detect sound and convert the detected sound into an electronic format (analog or digital). In the embodiment of FIG. 10, acoustic transducers 1020(I) and 1020(J) may be positioned on neckband 1005, thereby increasing the distance between the neckband acoustic transducers 1020(I) and 1020(J) and other acoustic transducers 1020 positioned on eyewear device 1002. In some cases, increasing the distance between acoustic transducers 1020 of the microphone array may improve the accuracy of beamforming performed via the microphone array. For example, if a sound is detected by acoustic transducers 1020(C) and 1020(D) and the distance between acoustic transducers 1020(C) and 1020(D) is greater than, e.g., the distance between acoustic transducers 1020(D) and 1020(E), the determined source location of the detected sound may be more accurate than if the sound had been detected by acoustic transducers 1020(D) and 1020(E).

Controller 1025 of neckband 1005 may process information generated by the sensors on neckband 1005 and/or augmented reality system 1000. For example, controller 1025 may process information from the microphone array that describes sounds detected by the microphone array. For each detected sound, controller 1025 may perform a direction-of-arrival (DOA) estimation to estimate a direction from which the detected sound arrived at the microphone array. As the microphone array detects sounds, controller 1025 may populate an audio data set with the information. In embodiments in which augmented reality system 1000 includes an inertial measurement unit, controller 1025 may compute all inertial and spatial calculations from the IMU located on eyewear device 1002. A connector may convey information between augmented reality system 1000 and neckband 1005 and between augmented reality system 1000 and controller 1025. The information may be in the form of optical data, electrical data, wireless data, or any other transmittable data form. Moving the processing of information generated by augmented reality system 1000 to neckband 1005 may reduce weight and heat in eyewear device 1002, making it more comfortable to the user.

Power source 1035 in neckband 1005 may provide power to eyewear device 1002 and/or to neckband 1005. Power source 1035 may include, without limitation, lithium ion batteries, lithium-polymer batteries, primary lithium batteries, alkaline batteries, or any other form of power storage. In some cases, power source 1035 may be a wired power source. Including power source 1035 on neckband 1005 instead of on eyewear device 1002 may help better distribute the weight and heat generated by power source 1035.

As noted, some artificial reality systems may, instead of blending an artificial reality with actual reality, substantially replace one or more of a user's sensory perceptions of the real world with a virtual experience. One example of this type of system is a head-worn display system, such as virtual reality system 1100 in FIG. 11, that mostly or completely covers a user's field of view. Virtual reality system 1100 may include a front rigid body 1102 and a band 1104 shaped to fit around a user's head. Virtual reality system 1100 may also include output audio transducers 1106(A) and 1106(B). Furthermore, while not shown in FIG. 11, front rigid body 1102 may include one or more electronic elements, including one or more electronic displays, one or more inertial measurement units (IMUS), one or more tracking emitters or detectors, and/or any other suitable device or system for creating an artificial reality experience.

Artificial reality systems may include a variety of types of visual feedback mechanisms. For example, display devices in augmented reality system 1000 and/or virtual reality system 1100 may include one or more liquid crystal displays (LCDs), light emitting diode (LED) displays, organic LED (OLED) displays, and/or any other suitable type of display screen. Artificial reality systems may include a single display screen for both eyes or may provide a display screen for each eye, which may allow for additional flexibility for varifocal adjustments or for correcting a user's refractive error. Some artificial reality systems may also include optical subsystems having one or more lenses (e.g., conventional concave or convex lenses, Fresnel lenses, adjustable liquid lenses, etc.) through which a user may view a display screen.

In addition to or instead of using display screens, some artificial reality systems may include one or more projection systems. For example, display devices in augmented reality system 1000 and/or virtual reality system 1100 may include micro-LED projectors that project light (using, e.g., a waveguide) into display devices, such as clear combiner lenses that allow ambient light to pass through. The display devices may refract the projected light toward a user's pupil and may enable a user to simultaneously view both artificial reality content and the real world. Artificial reality systems may also be configured with any other suitable type or form of image projection system.

Artificial reality systems may also include various types of computer vision components and subsystems. For example, augmented reality system 900, augmented reality system 1000, and/or virtual reality system 1100 may include one or more optical sensors, such as two-dimensional (2D) or 3D cameras, time-of-flight depth sensors, single-beam or sweeping laser rangefinders, 3D LiDAR sensors, and/or any other suitable type or form of optical sensor. An artificial reality system may process data from one or more of these sensors to identify a location of a user, to map the real world, to provide a user with context about real-world surroundings, and/or to perform a variety of other functions.

Artificial reality systems may also include one or more input and/or output audio transducers. In the examples shown in FIGS. 9 and 11, output audio transducers 908(A), 908(B), 1106(A), and 1106(B) may include voice coil speakers, ribbon speakers, electrostatic speakers, piezoelectric speakers, bone conduction transducers, cartilage conduction transducers, and/or any other suitable type or form of audio transducer. Similarly, input audio transducers 910 may include condenser microphones, dynamic microphones, ribbon microphones, and/or any other type or form of input transducer. In some embodiments, a single transducer may be used for both audio input and audio output.

Figure 11:
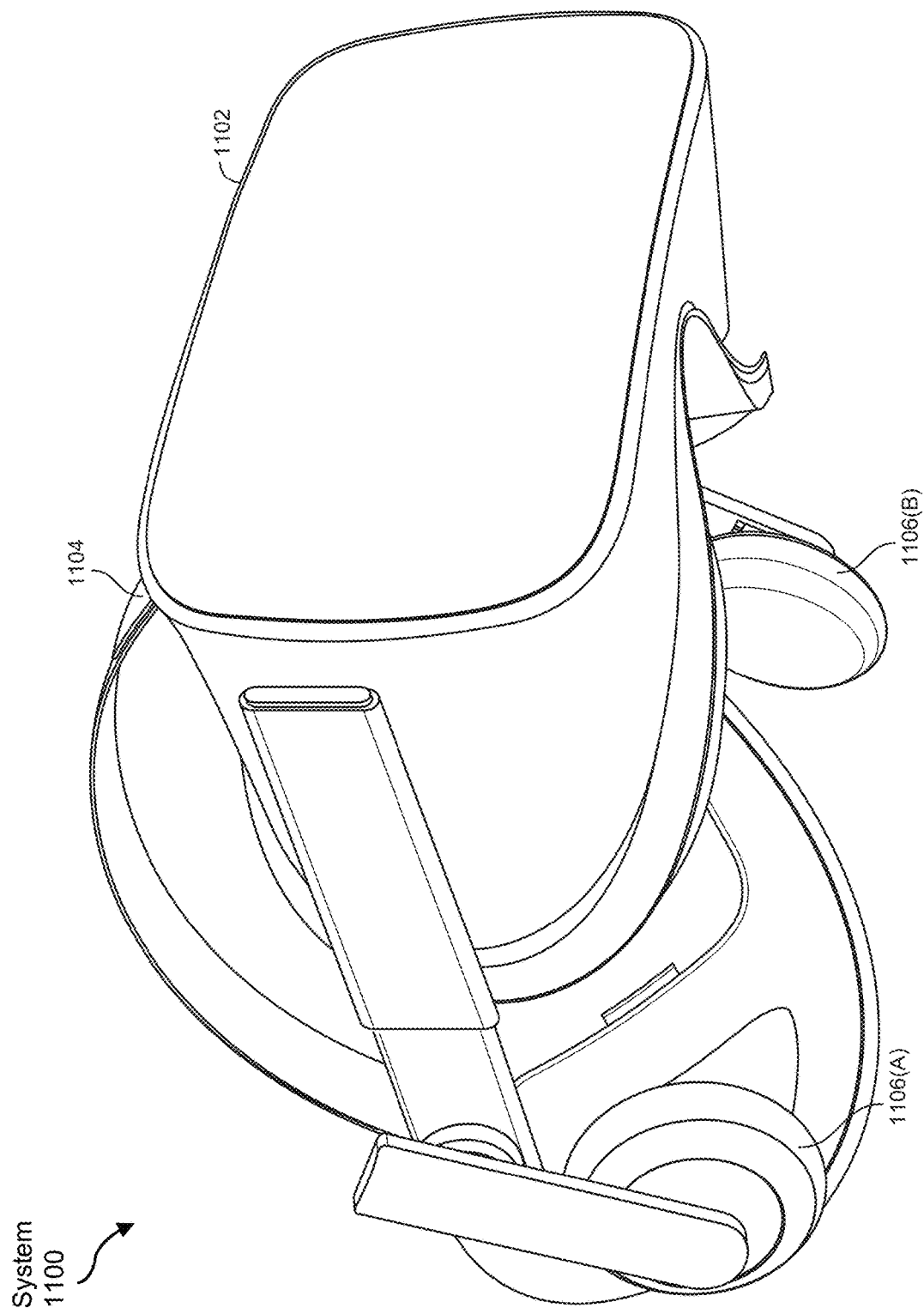
FIG. 11 is an illustration of an exemplary virtual reality headset that may be used in connection with embodiments of this disclosure.

While not shown in FIGS. 9-11, artificial reality systems may include tactile (i.e., haptic) feedback systems, which may be incorporated into headwear, gloves, body suits, handheld controllers, environmental devices (e.g., chairs, floormats, etc.), and/or any other type of device or system. Haptic feedback systems may provide various types of cutaneous feedback, including vibration, force, traction, texture, and/or temperature. Haptic feedback systems may also provide various types of kinesthetic feedback, such as motion and compliance. Haptic feedback may be implemented using motors, piezoelectric actuators, fluidic systems, and/or a variety of other types of feedback mechanisms. Haptic feedback systems may be implemented independent of other artificial reality devices, within other artificial reality devices, and/or in conjunction with other artificial reality devices.

By providing haptic sensations, audible content, and/or visual content, artificial reality systems may create an entire virtual experience or enhance a user's real-world experience in a variety of contexts and environments. For instance, artificial reality systems may assist or extend a user's perception, memory, or cognition within a particular environment. Some systems may enhance a user's interactions with other people in the real world or may enable more immersive interactions with other people in a virtual world. Artificial reality systems may also be used for educational purposes (e.g., for teaching or training in schools, hospitals, government organizations, military organizations, business enterprises, etc.), entertainment purposes (e.g., for playing video games, listening to music, watching video content, etc.), and/or for accessibility purposes (e.g., as hearing aids, visuals aids, etc.). The embodiments disclosed herein may enable or enhance a user's artificial reality experience in one or more of these contexts and environments and/or in other contexts and environments.

As noted, artificial reality systems 900, 1000, and 1100 may be used with a variety of other types of devices to provide a more compelling artificial reality experience. These devices may be haptic interfaces with transducers that provide haptic feedback and/or that collect haptic information about a user's interaction with an environment. The artificial reality systems disclosed herein may include various types of haptic interfaces that detect or convey various types of haptic information, including tactile feedback (e.g., feedback that a user detects via nerves in the skin, which may also be referred to as cutaneous feedback) and/or kinesthetic feedback (e.g., feedback that a user detects via receptors located in muscles, joints, and/or tendons).

Figure 12:
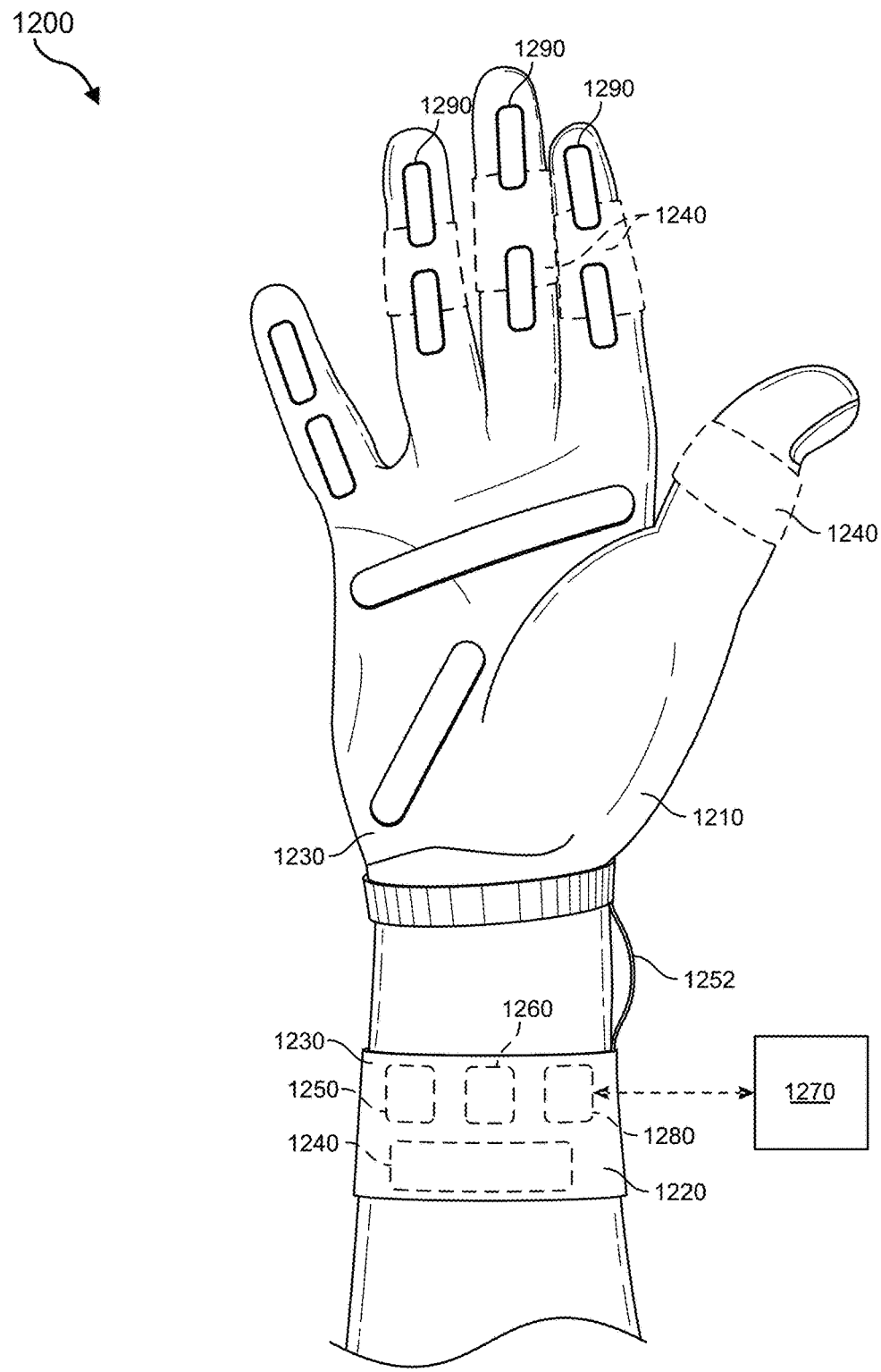
FIG. 12 is an illustration of exemplary haptic devices that may be used in connection with embodiments of this disclosure.

Haptic feedback may be provided by interfaces positioned within a user's environment (e.g., chairs, tables, floors, etc.) and/or interfaces on articles that may be worn or carried by a user (e.g., gloves, wristbands, etc.). As an example, FIG. 12 illustrates a vibrotactile system 1200 in the form of a wearable glove (haptic device 1210) and wristband (haptic device 1220). Haptic device 1210 and haptic device 1220 are shown as examples of wearable devices that include a flexible, wearable textile material 1230 that is shaped and configured for positioning against a user's hand and wrist, respectively. This disclosure also includes vibrotactile systems that may be shaped and configured for positioning against other human body parts, such as a finger, an arm, a head, a torso, a foot, or a leg. By way of example and not limitation, vibrotactile systems according to various embodiments of the present disclosure may also be in the form of a glove, a headband, an armband, a sleeve, a head covering, a sock, a shirt, or pants, among other possibilities. In some examples, the term "textile" may include any flexible, wearable material, including woven fabric, non-woven fabric, leather, cloth, a flexible polymer material, composite materials, etc.

One or more vibrotactile devices 1240 may be positioned at least partially within one or more corresponding pockets formed in textile material 1230 of vibrotactile system 1200. Vibrotactile devices 1240 may be positioned in locations to provide a vibrating sensation (e.g., haptic feedback) to a user of vibrotactile system 1200. For example, vibrotactile devices 1240 may be positioned to be against the user's finger(s), thumb, or wrist, as shown in FIG. 12. Vibrotactile devices 1240 may, in some examples, be sufficiently flexible to conform to or bend with the user's corresponding body part(s).

A power source 1250 (e.g., a battery) for applying a voltage to the vibrotactile devices 1240 for activation thereof may be electrically coupled to vibrotactile devices 1240, such as via conductive wiring 1252. In some examples, each of vibrotactile devices 1240 may be independently electrically coupled to power source 1250 for individual activation. In some embodiments, a processor 1260 may be operatively coupled to power source 1250 and configured (e.g., programmed) to control activation of vibrotactile devices 1240.

Vibrotactile system 1200 may be implemented in a variety of ways. In some examples, vibrotactile system 1200 may be a standalone system with integral subsystems and components for operation independent of other devices and systems. As another example, vibrotactile system 1200 may be configured for interaction with another device or system 1270. For example, vibrotactile system 1200 may, in some examples, include a communications interface 1280 for receiving and/or sending signals to the other device or system 1270. The other device or system 1270 may be a mobile device, a gaming console, an artificial reality (e.g., virtual reality, augmented reality, mixed reality) device, a personal computer, a tablet computer, a network device (e.g., a modem, a router, etc.), a handheld controller, etc. Communications interface 1280 may enable communications between vibrotactile system 1200 and the other device or system 1270 via a wireless (e.g., Wi-Fi, Bluetooth, cellular, radio, etc.) link or a wired link. If present, communications interface 1280 may be in communication with processor 1260, such as to provide a signal to processor 1260 to activate or deactivate one or more of the vibrotactile devices 1240.

Vibrotactile system 1200 may optionally include other subsystems and components, such as touch-sensitive pads 1290, pressure sensors, motion sensors, position sensors, lighting elements, and/or user interface elements (e.g., an on/off button, a vibration control element, etc.). During use, vibrotactile devices 1240 may be configured to be activated for a variety of different reasons, such as in response to the user's interaction with user interface elements, a signal from the motion or position sensors, a signal from the touch-sensitive pads 1290, a signal from the pressure sensors, a signal from the other device or system 1270, etc.

Although power source 1250, processor 1260, and communications interface 1280 are illustrated in FIG. 12 as being positioned in haptic device 1220, the present disclosure is not so limited. For example, one or more of power source 1250, processor 1260, or communications interface 1280 may be positioned within haptic device 1210 or within another wearable textile.

Figure 13:
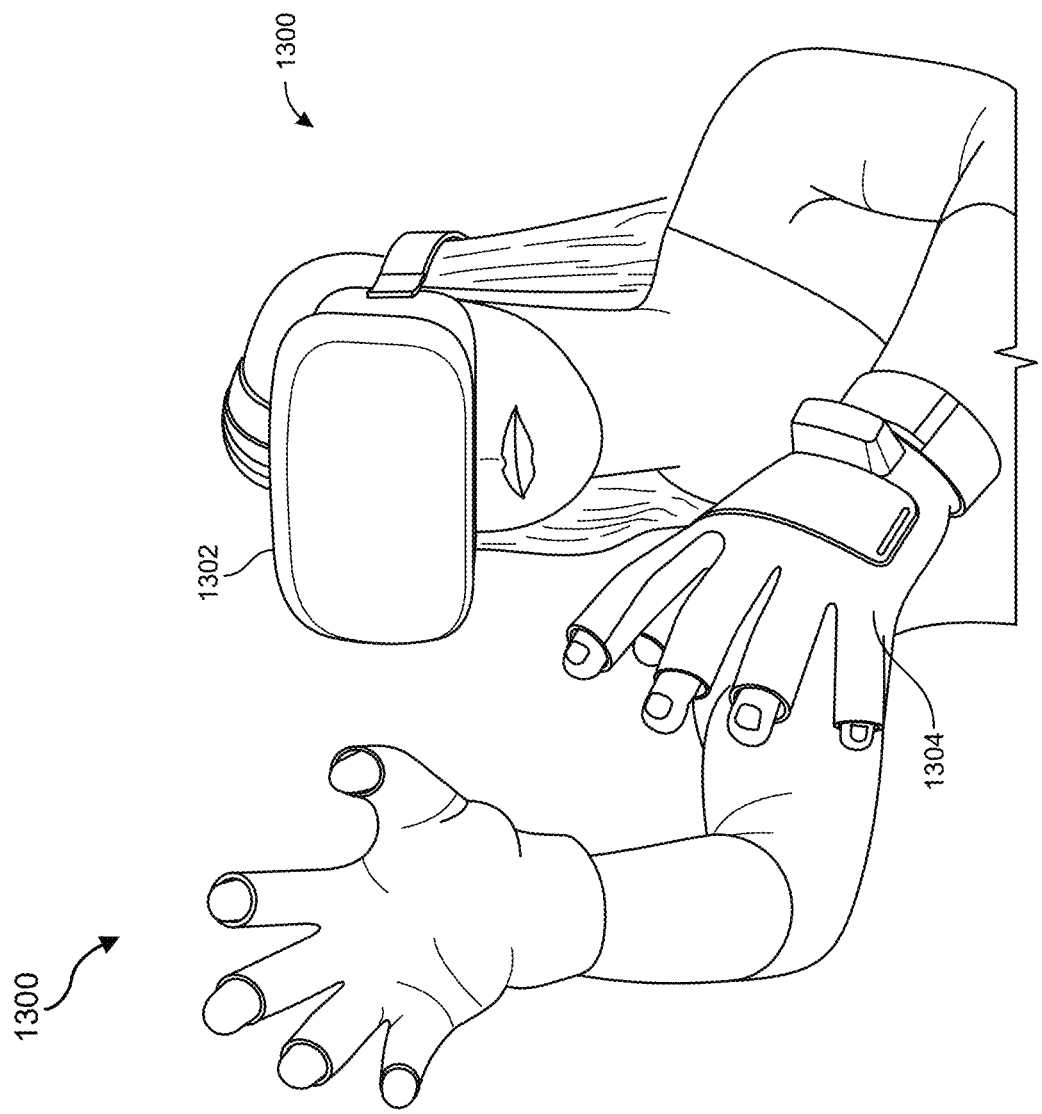
FIG. 13 is an illustration of an exemplary virtual reality environment according to embodiments of this disclosure.

Haptic wearables, such as those shown in and described in connection with FIG. 12, may be implemented in a variety of types of artificial reality systems and environments. FIG. 13 shows an example artificial reality environment 1300 including one head-mounted virtual reality display and two haptic devices (i.e., gloves), and in other embodiments any number and/or combination of these components and other components may be included in an artificial reality system. For example, in some embodiments there may be multiple head-mounted displays each having an associated haptic device, with each head-mounted display and each haptic device communicating with the same console, portable computing device, or other computing system.

Head-mounted display 1302 generally represents any type or form of virtual reality system, such as virtual reality system 1000 in FIG. 10. Haptic device 1304 generally represents any type or form of wearable device, worn by a use of an artificial reality system, that provides haptic feedback to the user to give the user the perception that he or she is physically engaging with a virtual object. In some embodiments, haptic device 1304 may provide haptic feedback by applying vibration, motion, and/or force to the user. For example, haptic device 1304 may limit or augment a user's movement. To give a specific example, haptic device 1304 may limit a user's hand from moving forward so that the user has the perception that his or her hand has come in physical contact with a virtual wall. In this specific example, one or more actuators within the haptic advice may achieve the physical-movement restriction by pumping fluid into an inflatable bladder of the haptic device. In some examples, a user may also use haptic device 1304 to send action requests to a console. Examples of action requests include, without limitation, requests to start an application and/or end the application and/or requests to perform a particular action within the application.

Figure 14:
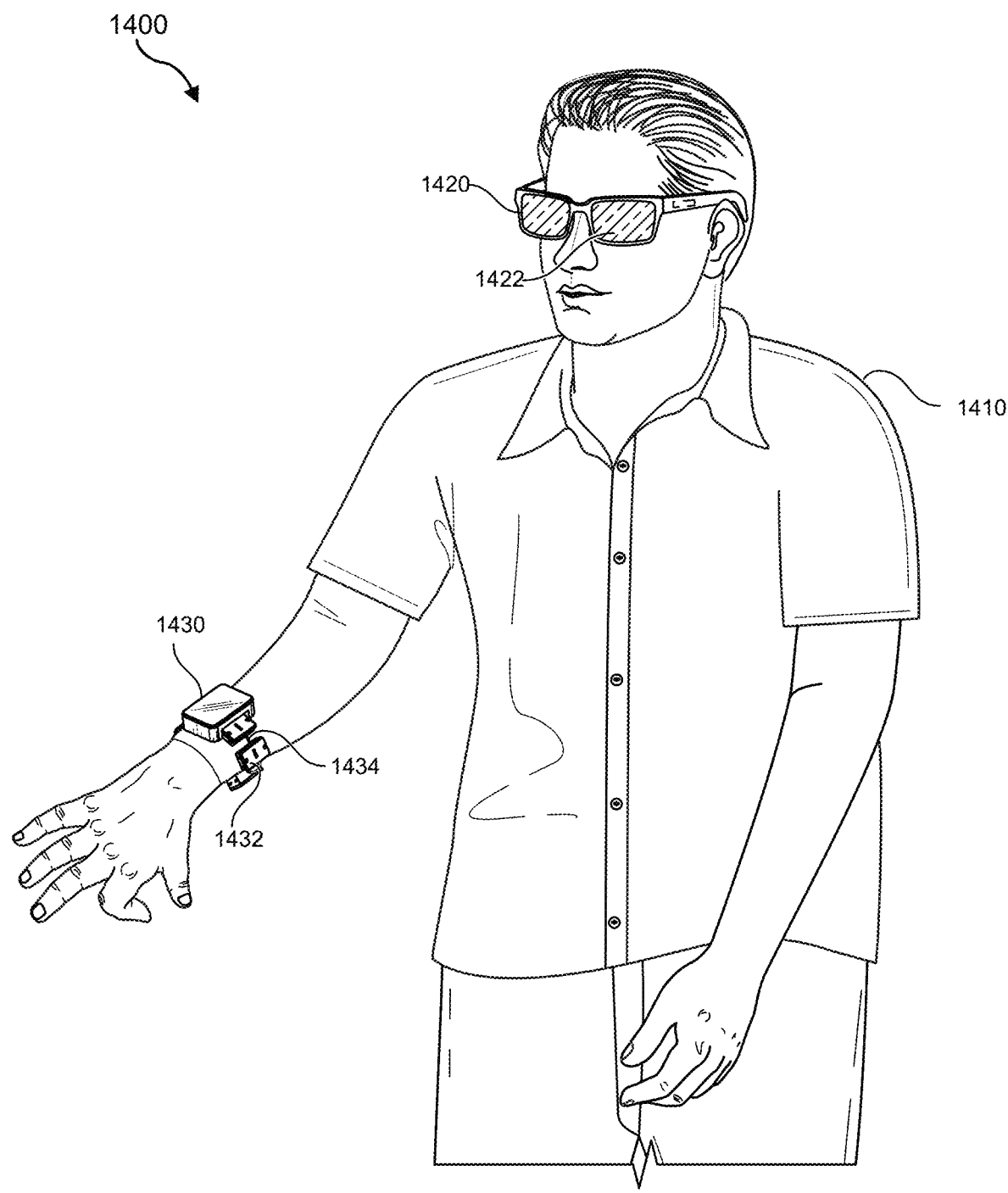
FIG. 14 is an illustration of an exemplary augmented reality environment according to embodiments of this disclosure.

While haptic interfaces may be used with virtual reality systems, as shown in FIG. 13, haptic interfaces may also be used with augmented reality systems, as shown in FIG. 14. FIG. 14 is a perspective view a user 1410 interacting with an augmented reality system 1400. In this example, user 1410 may wear a pair of augmented reality glasses 1420 that have one or more displays 1422 and that are paired with a haptic device 1430. Haptic device 1430 may be a wristband that includes a plurality of band elements 1432 and a tensioning mechanism 1434 that connects band elements 1432 to one another.

One or more of band elements 1432 may include any type or form of actuator suitable for providing haptic feedback. For example, one or more of band elements 1432 may be configured to provide one or more of various types of cutaneous feedback, including vibration, force, traction, texture, and/or temperature. To provide such feedback, band elements 1432 may include one or more of various types of actuators. In one example, each of band elements 1432 may include a vibrotactor (e.g., a vibrotactile actuator) configured to vibrate in unison or independently to provide one or more of various types of haptic sensations to a user. Alternatively, only a single band element or a subset of band elements may include vibrotactors.

Haptic devices 1210, 1220, 1304, and 1430 may include any suitable number and/or type of haptic transducer, sensor, and/or feedback mechanism. For example, haptic devices 1210, 1220, 1304, and 1430 may include one or more mechanical transducers, piezoelectric transducers, and/or fluidic transducers. Haptic devices 1210, 1220, 1304, and 1430 may also include various combinations of different types and forms of transducers that work together or independently to enhance a user's artificial-reality experience. In one example, each of band elements 1432 of haptic device 1430 may include a vibrotactor (e.g., a vibrotactile actuator) configured to vibrate in unison or independently to provide one or more of various types of haptic sensations to a user.

The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "comprising."

What is claimed is:

1. A cartilage conduction system comprising:
    a transducer that generates mechanical energy; and
    a functionally graded material (FGM) interface dimensioned to be coupled between the transducer and cartilage located on an outer ear of a user, wherein the FGM interface:
        exhibits a gradation of at least one characteristic from one side of the FGM interface that is impedance-matched to the transducer to another side of the FGM interface that is impedance-matched to the cartilage located on the outer ear of the user; and
        facilitates transferring the mechanical energy across the gradation of the characteristic from the transducer to the cartilage.

2. The cartilage conduction system of claim 1, wherein the FGM interface comprises a plurality of discrete material layers that collectively form the gradation of the characteristic exhibited by the FGM interface.

3. The cartilage conduction system of claim 1, wherein the gradation of the characteristic exhibited by the FGM interface comprises a specific gradient of the characteristic from the one side to the another side along one dimension of the FGM interface.

4. The cartilage conduction system of claim 1, wherein the characteristic comprises at least one of:
    stiffness;
    loss factor;
    density;
    lattice spacing;
    porosity;
    Poisson's ratio; or
    filler content.

5. The cartilage conduction system of claim 1, wherein:
    the one side of the FGM interface is coupled to the transducer;
    the another side of the FGM interface is dimensioned to be coupled to the cartilage located on the outer ear of the user;
    the one side of the FGM interface has a first stiffness modulus; and
    the another side of the FGM interface has a second stiffness modulus that is lower than the first stiffness modulus.

6. The cartilage conduction system of claim 1, wherein the another side of the FGM interface contours to the cartilage located on the outer ear of the user.

7. The cartilage conduction system of claim 1, wherein the FGM interface is dimensioned to be coupled between the transducer and at least one of:
    a portion of a helix of the user;
    a tragus of the user;
    an antihelix of the user;
    a scapha of the user;
    a scaphoid fossa of the user; or
    a concha of the user.

8. The cartilage conduction system of claim 1, wherein the transducer generates vibrations that:
    are transferred to the cartilage located on the outer ear of the user via the FGM interface; and
    cause the cartilage to generate sound pressure that propagates to an eardrum of the user.

9. The cartilage conduction system of claim 1, wherein the FGM interface is anisotropic such that:
    the FGM interface exhibits a first level of transmissibility in a direction from the transducer to the cartilage; and
    the FGM interface exhibits a second level of transmissibility in an opposite direction from the cartilage to the transducer, the second level of transmissibility being lower than the first level of transmissibility.

10. The cartilage conduction system of claim 9, wherein:
    the mechanical energy comprises vibrations;
    the cartilage generates sound pressure from the vibrations; and
    the FGM interface prevents at least some of the vibrations from returning to the transducer in the opposite direction due at least in part to the second level of transmissibility being lower than the first level of transmissibility.

11. The cartilage conduction system of claim 1, further comprising an FGM suppressor that at least partially encompasses a portion of the transducer coupled to the FGM interface, wherein the FGM suppressor:
    exhibits an additional gradation of at least one additional characteristic from the one side of the FGM suppressor to the another side of the FGM suppressor; and
    mitigates leakage of the mechanical energy generated by the transducer to an environment of the user.

12. The cartilage conduction system of claim 11, wherein the gradation of the characteristic exhibited by the FGM interface and the additional gradation of the characteristic exhibited by the FGM suppressor differ from one another.

13. The cartilage conduction system of claim 11, wherein the additional gradation of the characteristic exhibited by the FGM suppressor comprises a specific gradient of loss factor from the one side of the FGM suppressor to the another side of the FGM suppressor along one dimension.

14. The cartilage conduction system of claim 1, wherein the FGM interface is 3D-printed.

15. An artificial reality system comprising:
a head-mounted display; and
a cartilage conduction device communicatively coupled to the head-mounted display, wherein the cartilage conduction device comprises:
  a transducer that generates mechanical energy; and
  a functionally graded material (FGM) interface dimensioned to be coupled between the transducer and cartilage located on an outer ear of a user, wherein the FGM interface:
    exhibits a gradation of at least one characteristic from one side of the FGM interface that is impedance-matched to the transducer to another side of the FGM interface that is impedance-matched to the cartilage located on the outer ear of the user; and
    facilitates transferring the mechanical energy across the gradation of the characteristic from the transducer to the cartilage.

16. The artificial reality system of claim 15, wherein the FGM interface comprises a plurality of discrete material layers that form the gradation of the characteristic exhibited by the FGM interface.

17. The artificial reality system of claim 15, wherein the gradation of the characteristic exhibited by the FGM interface comprises a specific gradient of the characteristic from the one side to the another side along one dimension of the FGM interface.

18. The artificial reality system of claim 15, wherein the characteristic comprises at least one of:
stiffness;
loss factor;
density;
lattice spacing;
porosity;
Poisson's ratio; or
filler content.

19. A method comprising:
manufacturing a functionally graded material (FGM) interface that:
  exhibits a gradation of at least one characteristic from one side of the FGM interface that is impedance-matched to a transducer that generates mechanical energy to another side of the FGM interface that is impedance-matched to cartilage located on an outer ear of a user; and
  is dimensioned to be coupled to the cartilage located on the outer ear of the user; and
coupling the FGM interface to the transducer to enable the FGM interface to facilitate transferring the mechanical energy across the gradation of the characteristic from the transducer to the cartilage.

* * * * *